(12) United States Patent
Guegler et al.

(10) Patent No.: US 6,391,606 B1
(45) Date of Patent: May 21, 2002

(54) ISOLATED HUMAN PHOSPHOLIPASE PROTEINS, NUCLEIC ACID MOLECULES ENCODING HUMAN PHOSPHOLIPASE PROTEINS, AND USES THEREOF

(75) Inventors: Karl Guegler, Menlo Park, CA (US); Ellen M. Beasley, Darnestown, MD (US); Karen A. Ketchum, Germantown, MD (US); Valentina Di Francesco, Rockville, MD (US)

(73) Assignee: PE Corporation, Norwalk, CT (US)

( * ) Notice: Subject to any disclaimer, the term of this patent is extended or adjusted under 35 U.S.C. 154(b) by 0 days.

(21) Appl. No.: 09/738,884

(22) Filed: Dec. 18, 2000

Related U.S. Application Data
(60) Provisional application No. 60/232,632, filed on Sep. 14, 2000.

(51) Int. Cl.[7] .............. C12N 9/20; C12N 1/20; C12N 1/68; C12P 21/04; C07H 21/04
(52) U.S. Cl. .......... 435/198; 435/252.3; 435/370.1; 435/71.1; 435/6; 435/325; 536/23.2
(58) Field of Search .............. 435/198, 252.3, 435/71.1, 6, 325; 536/23.2

Primary Examiner—Ponnathapu Achutamurthy
Assistant Examiner—Yong Pak
(74) Attorney, Agent, or Firm—Celera Genomics; Justin D. Karjala

(57) ABSTRACT

The present invention provides amino acid sequences of peptides that are encoded by genes within the human genome, the phospholipase peptides of the present invention. The present invention specifically provides isolated peptide and nucleic acid molecules, methods of identifying orthologs and paralogs of the phospholipase peptides, and methods of identifying modulators of the phospholipase peptides.

10 Claims, 17 Drawing Sheets

```
   1 ATGGGCCTGA CGGAGGACGA GGACGTGCGC GCCATGCTGC GGGGCTCCCG
  51 GCTCCGCAAG ATCCGCTCGC GCACGTGGCA CAAGGAGCGG CTGTACCGGC
 101 TGCAGGAGGA CGGCCTGAGC GTGTGGTTCC AGCGCGCGAT CCCGCGTGCG
 151 CCATCGCAGC ACATCTTCTT CGTGCAGCAC ATCGAGGCGG TCCGCGAGGG
 201 CCACCAGTCC GAGGGCCTGC GGCGCTTCGG GGGTGCCTTC GCGCCAGCGC
 251 GCTGCCTCAC CATCGCCTTC AAGGGCCGCC GCAAGAACCT GGACCTGGCG
 301 GCGCCCACGG CTGAGGAAGC GCAGCGCTGG GTGCGCGGTC TGACCAAGCT
 351 CCGCGCGCGC CTGGACGCCA TGAGCCAGCG CGAGCGGCTA GACCACTGGA
 401 TCCACTCCTA TCTGCACCGG GCTGACTCCA ACCAGGACAG CAAGATGAGC
 451 TTCAAGGAGA TCAAGAGCCT GCTGAGAATG GTCAACGTGG ACATGAACGA
 501 CATGTACGCC TACCTCCTCT TCAAGGAGTG TGACCACTCC AACAACGACC
 551 GTCTAGAGGG GGCTGAGATC GAGGAGTTCC TGCGGCGGCT GCTGAAGCGG
 601 CCGGAGCTGG AGGAGATCTT CCATCAGTAC TCGGGCGAGG ACCGCGTGCT
 651 GAGTGCCCCT GAGCTGCTGG AGTTCCTGGA GGACCAGGGC GAGGAGGGCG
 701 CCACACTGGC CCGCGCCCAG CAGCTCATTC AGACCTATGA GCTCAACGAG
 751 ACAGCCAAGC AGCATGAGCT GATGACACTG GATGGCTTCA TGATGTTACCT
 801 GTTGTCGCCG GAGGGGACTG CCTTGGACAA CACCCACACG TGTGTGTTCC
 851 AGGACATGAA CCAGCCCCTT GCCCACTACT TCATCTCTTC CTCCCACAAC
 901 ACCTATCTGA CTGACTCCCA GATCGGGGGG CCCAGCAGCA CCGAGGCCTA
 951 TGTTAGGGCC TTTGCCCAGG GATGCCGCTG CGTGGAGCTG GACTGCTGGG
1001 AGGGGCCAGG AGGGGAGCCC GTCATCTATC ATGGCCATAC CCTCACCTCC
1051 AAGATTCTCT TCCGGGACGT GGCCCAAGCC GTGCGGCAGC ATGCCTTCAC
1101 GCTGTCCCCT TACCCTGTCA TCCTATCCCT GGAGAACCAC TGCCGGGCTGG
1151 AGCAGCAGGC TGCCATGGCC CGCCACCTCT GCACCATCCT GGGGGACATG
1201 CTGGTGACAC AGGCGCTGGA CTCCCCAAAT CCCGAGGAGC TGCCATCCCC
1251 AGAGCAGCTG AGGGCCGGG TCCTGGTGAA GGGAAAGAAG CTGCCCGCTG
1301 CTCGGAGCGA GGATGGCCGG GCTCTGTCGG ATCGGGAGGA GGGGGAGGAG
1351 GATGACGAGG AGGAAGAAGA GGAGGTGGAG GCTGCAGCGC AAGAGCGGCT
1401 GGCCAAGCAG ATCTCCCCGG AGCTGTCGGC CCTGGCTGTG TACTGCCACG
1451 CCACCCGCCT GCGGACCCTG CACCCTGCCC CCAACGCCCC ACAACCCTGC
1501 CAGGTCAGCT CCCTCAGCGA GCGCAAAGCC AAGAAACTCA TTCGGGAGGC
1551 AGGGAACAGC TTTGTCAGGC ACAATGCCCG CCAGCTGACC CGCGTGTACC
1601 CGCTGGGGCT GCGGATGAAC TCAGCCAACT ACGATCCCCA GGAGATGTGG
1651 AACTCGGGCT GTCAGCTGGT GGCCTTGAAC TTCCAGACGC CAGGCTACGA
1701 GATGGACCTC AATGCCGGGC GCTTCCTAGT CAATGGGCAG TGTGGCTACG
1751 TCCTAAAACC TGCCTGCCTG CGGCAACCTG ACTCGACCTT TGACCCCGAG
1801 TACCCAGGAC CTCCCAGAAC CACTCTCAGC ATCCAGGTGC TGACTGCACA
1851 GCAGCTGCCC AAGCTGAATG CCGAGAAGCC ACACTCCATT GTGGACCCCC
1901 TGGTGCGCAT TGAGATCCAT GGGGTGCCCG CAGCTGTGC CCGGCAGGAG
1951 ACTGACTACG TGCTCAACAA TGGCTTCAAC CCCCGCTGGG GGCAGACCCT
2001 GCAGTTCCAG CTGCGGGCTC CGGAGCTGGC ACTGGTCCGG TTTGTGGTGG
2051 AAGATTATGA CGCCACCTCC CCCAATGACT TTGTGGGCCA GTTTACACTG
2101 CCTCTTAGCA GCCTAAAGCA AGGGTACCGC CACATACACC TGCTTTCCAA
2151 GGACGGGGCC TCACTGTCAC CAGCCACGCT CTTCATCCAA ATCCGCATCC
2201 AGCGCTCCTG A (SEQ ID NO:1)
```

FEATURES:
Start Codon: 1
Stop Codon: 2209
3'UTR: 2212

Homologous proteins:
Top BLAST Hits

```
                                                                     Score   E
gi|2137061|pir||PC4183 1-phosphatidylinositol-4,5-bisphosphate ...    776   0.0
gi|9790167|ref|NP_062650.1| phospholipase C, delta; PLC-delta 1...    761   0.0
gi|2143912|pir||I55942 phospholipase C-delta (EC 3.1.4.-), muta...    761   0.0
gi|5453910|ref|NP_006216.1| phospholipase C, delta 1 [Homo sapi...    760   0.0
gi|8393981|ref|NP_058731.1| phospholipase C-delta1 [Rattus norv...    755   0.0
gi|1150520|emb|CAA89822.1| (Z49747) phospholipase C [Oryctolagu...    754   0.0
gi|130227|sp|P10895|PIP6_BOVIN 1-PHOSPHATIDYLINOSITOL-4,5-BISPH...    721   0.0
gi|89332|pir||C28821 1-phosphatidylinositol-4,5-bisphosphate ph...     720   0.0
gi|108854|pir||S14113 1-phosphatidylinositol-4,5-bisphosphate p...    710   0.0
gi|571466|gb|AAC52346.1| (U16655) phospholipase C delta-4 [Ratt...    664   0.0
gi|1304189|dbj|BAA09046.1| (D50455) phodpholipase C delta4 [Rat...    647   0.0
gi|2392276|pdb|1DJX|B Chain B, Phosphoinositide-Specific Phosph...    647   0.0
gi|1942319|pdb|1QAT|A Chain A, 1-Phosphatidylinositol-4,5-Bisph...    646   0.0
```

BLAST to dbEST:

```
                                         Score   E
gi|9897953  /dataset=dbest /taxon=960...  1225   0.0
gi|10210099 /dataset=dbest /taxon=96...   1193   0.0
gi|11295787 /dataset=dbest /taxon=96...   1183   0.0
gi|11061367 /dataset=dbest /taxon=96...   1122   0.0
gi|9772144  /dataset=dbest /taxon=9606...  1108   0.0
gi|10150191 /dataset=dbest /taxon=96...   1029   0.0
gi|9323477  /dataset=dbest /taxon=960...  1021   0.0
gi|10322141 /dataset=dbest /taxon=96...    961   0.0
gi|9122991  /dataset=dbest /taxon=9606...   868   0.0
gi|9773286  /dataset=dbest /taxon=9606...   856   0.0
```

EXPRESSION INFORMATION FOR MODULATORY USE:
library source:
Expression information from BLAST dbEST hits
gi|9897953   Panceras adenocarcinoma
gi|10210099  Lung
gi|11295787  Brain anaplastic oligodendroglioma
gi|11061367  Lung
gi|9772144   Placenta choriocarcinoma
gi|10150191  Panceas adenocarcinoma
gi|9323477   uterus endometrium
gi|10322141  Colon adenocarcinoma
gi|9122991   eye retinoblastoma
gi|9773286   Placenta choriocarcinoma Expression information from PCR-based tissue screening panels:
Fetal whole brain

```
   1 ATGGGCCTGA CGGAGGACGA GGACGTGCGC GCCATGCTGC GGGGCTCCCG
  51 GCTCCGCAAG ATCCGCTCGC GCACGTGGCA CAAGGAGCGG CTGTACCGGC
 101 TGCAGGAGGA CGGCCTGAGC GTGTGGTTCC AGCGGCGCAT CCCGCGTGCG
 151 CCATCGCAGC ACATCTTCTT CGTGCAGCAC ATCGAGGCGG TCCGCGAGGG
 201 CCACCAGTCC GAGGGCCTGC GGCGCTTCGG GGGTGCCTTC GCGCCAGCGC
 251 GCTGCCTCAC CATCGCCTTC AAGGGCCGCC GCAAGAACCT GGACCTGGCG
 301 GCGCCCACGG CTGAGGAAGC GCAGCGCTGG GTGCGCGGTC TGACCAAGCT
 351 CCGCGCGCGC CTGGACGCCA TGAGCCAGCG CGAGCGGCTA GACCACTGGA
 401 TCCACTCCTA TCTGCACCGG GCTGACTCCA ACCAGGACAG CAAGATGAGC
 451 TTCAAGGAGA TCAAGAGCCT GCTGAGAATG GTCAACGTGG ACATGAACGA
 501 CATGTACGCC TACCTCCTCT TCAAGGAGTG TGACCACTCC AACAACGACC
 551 GTCTAGAGGG GGCTGAGATC GAGGAGTTCC TGCGGCGGCT GCTGAAGCGG
 601 CCGGAGCTGG AGGAGATCTT CCATCAGTAC TCGGGCGAGG ACCGCGTGCT
 651 GAGTGCCCCT GAGCTGCTGG AGTTCCTGGA GGACCAGGGC GAGGAGGGCG
 701 CCACACTGGC CCGCGCCCAG CAGCTCATTC AGACCTATGA GCTAACGAG
 751 ACAGCCAAGC AGCATGAGCT GATGACACTG GATGGCTTCA TGATGTACCT
 801 GTTGTCGCCG GAGGGGACTG CCTTGGACAA CACCCACACG TGTGTGTTCC
 851 AGGACATGAA CCAGCCCCTT GCCCACTACT TCATCTCTTC CTCCCACAAC
 901 ACCTATCTGA CTGACTCCCA GATCGGGGGG CCCAGCAGCA CCGAGGCCTA
 951 TGTTAGGGCC TTTGCCCAGG GATGCCGCTG CGTGGAGCTG GACTGCTGGG
1001 AGGGGCCAGG AGGGGAGCCC GTCATCTATC ATGGCCATAC CCTCACCTCC
1051 AAGATTCTCT TCCGGGACGT GGCCCAAGCC GTGCGCGACC ATGCCTTCAC
1101 GCTGTCCCCT TACCCTGTCA TCCTATCCCT GGAGAACCAC TGCGGGCTGG
1151 AGCAGCAGGC TGCCATGGCC CGCCACCTCT GCACCATCCT GGGGACATG
1201 CTGGTGACAC AGGCGCTGGA CTCCCCAAAT CCCGAGGAGC TGCCATCCCC
1251 AGAGCAGCTG AAGGGCCGGG TCCTGGTGAA GGGAAAGAAG CTGCCCGCTG
1301 CTCGGAGCGA GGATGGCCGG GCTCTGTCGG ATCGGGAGGA GGGGGAGGAG
1351 GATGACGAGG AGGAAGAAGA GGAGGTGGAG GCTGCAGCGC AGAGGCGGCT
1401 GGCCAAGCAG ATCTCCCCGG AGCTGTCGGC CCTGGCTGTG TACTGCCACG
1451 CCACCCGCCT GCGGACCCTG CACCCTGCCC CAACGCCCC ACAACCCTGC
1501 CAGGTCAGCT CCCTCAGCGA GCGCAAAGCC AAGAAACTCA TTCGGGAGGC
1551 AGGGAACAGC TTTGTCAGGC ACAATGCCCG CCAGCTGACC CGCGTGTACC
1601 CGCTGGGGCT GCGGATGAAC TCAGCCAACT ACAGTCCCCA GGAGATGTGG
1651 AACTCGGGCT GTCAGCTGGT GGCCTTGAAC TTCCAGACGC CAGGCTACGA
1701 GATGGACCTC AATGCCGGGC GCTTCCTAGT CAATGGGCAG TGTGGCTACG
1751 TCCTAAAACC TGCCTGCCTG CGGCAACCTG ACTCGACCTT TGACCCCGAG
1801 TACCCAGGAC CTCCCAGAAC CACTCTCAGC ATCCAGGTGC TGACTGCACA
1851 GCAGCTGCCC AAGCTGAATG CCGAGAAGCC ACACTCCATT GTGGACCCCC
1901 TGGTGCGCAT TGAGATCCAT GGGGTGCCCG CAGACTGTGC CCGGCAGGAG
1951 ACTGACTACG TGCTCAACAA TGGCTTCAAC CCCCGCTGGG GGCAGACCCT
2001 GCAGTTCCAG CTGCGGGCTC CGGAGCTGGC ACTGGTCCGG TTTGTGGTGG
2051 AAGATTATGA CGCCACCTCC CCCAATGACT TTGTGGGCCA GTTTACACTG
2101 CCTCTTAGCA GCCTAAAGCA AGGGTACCGC CACATACACC TGCTTTCCAA
2151 GGACGGGGCC TCACTGTCAC CAGCCACGCT CTTCATCCAA ATCCGCATCC
2201 AGCGCTCCTG A (SEQ ID NO:1)
```

FEATURES:
Start Codon: 1
Stop Codon: 2209
3'UTR: 2212

FIGURE 1A

Homologous proteins:
Top BLAST Hits

```
                                                                    Score    E
gi|2137061|pir||PC4183 1-phosphatidylinositol-4,5-bisphosphate ...   776    0.0
gi|9790167|ref|NP_062650.1| phospholipase C, delta; PLC-delta 1...  761    0.0
gi|2143912|pir||I55942 phospholipase C-delta (EC 3.1.4.-), muta...   761    0.0
gi|5453910|ref|NP_006216.1| phospholipase C, delta 1 [Homo sapi...   760    0.0
gi|8393981|ref|NP_058731.1| phospholipase C-delta1 [Rattus norv...   755    0.0
gi|1150520|emb|CAA89822.1| (Z49747) phospholipase C [Oryctolagu...    754    0.0
gi|130227|sp|P10895|PIP6_BOVIN 1-PHOSPHATIDYLINOSITOL-4,5-BISPH...    721    0.0
gi|89332|pir||C28821 1-phosphatidylinositol-4,5-bisphosphate ph...    720    0.0
gi|108854|pir||S14113 1-phosphatidylinositol-4,5-bisphosphate p...    710    0.0
gi|571466|gb|AAC52346.1| (U16655) phospholipase C delta-4 [Ratt...    664    0.0
gi|1304189|dbj|BAA09046.1| (D50455) phodpholipase C delta4 [Rat...    647    0.0
gi|2392276|pdb|1DJX|B Chain B, Phosphoinositide-Specific Phosph...    647    0.0
gi|1942319|pdb|1QAT|A Chain A, 1-Phosphatidylinositol-4,5-Bisph...    646    0.0
```

BLAST to dbEST:

```
                                          Score    E
gi|9897953  /dataset=dbest /taxon=960...  1225   0.0
gi|10210099 /dataset=dbest /taxon=96...   1193   0.0
gi|11295787 /dataset=dbest /taxon=96...   1183   0.0
gi|11061367 /dataset=dbest /taxon=96...   1122   0.0
gi|9772144  /dataset=dbest /taxon=9606... 1108   0.0
gi|10150191 /dataset=dbest /taxon=96...   1029   0.0
gi|9323477  /dataset=dbest /taxon=960...  1021   0.0
gi|10322141 /dataset=dbest /taxon=96...    961   0.0
gi|9122991  /dataset=dbest /taxon=9606...  868   0.0
gi|9773286  /dataset=dbest /taxon=9606...  856   0.0
```

EXPRESSION INFORMATION FOR MODULATORY USE:
library source:
Expression information from BLAST dbEST hits
gi|9897953   Panceras adenocarcinoma
gi|10210099  Lung
gi|11295787  Brain anaplastic oligodendroglioma
gi|11061367  Lung
gi|9772144   Placenta choriocarcinoma
gi|10150191  Panceas adenocarcinoma
gi|9323477   uterus endometrium
gi|10322141  Colon adenocarcinoma
gi|9122991   eye retinoblastoma
gi|9773286   Placenta choriocarcinoma Expression information from PCR-based tissue screening panels:
Fetal whole brain

FIGURE 1B

```
  1 MGLTEDEDVR AMLRGSRLRK IRSRTWHKER LYRLQEDGLS VWFQRRIPRA
 51 PSQHIFFVQH IEAVREGHQS EGLRRFGGAF APARCLTIAF KGRRKNLDLA
101 APTAEEAQRW VRGLTKLRAR LDAMSQRERL DHWIHSYLHR ADSNQDSKMS
151 FKEIKSLLRM VNVDMNDMYA YLLFKECDHS NNDRLEGAEI EEFLRRLLKR
201 PELEEIFHQY SGEDRVLSAP ELLEFLEDQG EEGATLARAQ QLIQTYELNE
251 TAKQHELMTL DGFMMYLLSP EGTALDNTHT CVFQDMNQPL AHYFISSSHN
301 TYLTDSQIGG PSSTEAYVRA FAQGCRCVEL DCWEGPGGEP VIYHGHTLTS
351 KILFRDVAQA VRDHAFTLSP YPVILSLENH CGLEQQAAMA RHLCTILGDM
401 LVTQALDSPN PEELPSPEQL KGRVLVKGKK LPAARSEDGR ALSDREEGEE
451 DDEEEEEEVE AAAQRRLAKQ ISPELSALAV YCHATRLRTL HPAPNAPQPC
501 QVSSLSERKA KKLIREAGNS FVRHNARQLT RVYPLGLRMN SANYSPQEMW
551 NSGCQLVALN FQTPGYEMDL NAGRFLVNGQ CGYVLKPACL RQPDSTFDPE
601 YPGPPRTTLS IQVLTAQQLP KLNAEKPHSI VDPLVRIEIH GVPADCARQE
651 TDYVLNNGFN PRWGQTLQFQ LRAPELALVR FVVEDYDATS PNDFVGQFTL
701 PLSSLKQGYR HIHLLSKDGA SLSPATLFIQ IRIQRS (SEQ ID NO:2)
```

FEATURES:
Functional domains and key regions:
[1] PDOC00001 PS00001 ASN_GLYCOSYLATION
N-glycosylation site 249-252 NETA

[2] PDOC00005 PS00005 PKC_PHOSPHO_SITE
Protein kinase C phosphorylation site

Number of matches: 7
    1    125-127 SQR
    2    150-152 SFK
    3    251-253 TAK
    4    349-351 TSK
    5    443-445 SDR
    6    506-508 SER
    7    704-706 SLK

[3] PDOC00006 PS00006 CK2_PHOSPHO_SITE
Casein kinase II phosphorylation site

Number of matches: 16
    1      4-7 TEDE
    2    103-106 TAEE
    3    125-128 SQRE
    4    143-146 SNQD
    5    150-153 SFKE
    6    180-183 SNND
    7    211-214 SGED
    8    218-221 SAPE
    9    273-276 TALD
   10    312-315 SSTE
   11    443-446 SDRE
   12    504-507 SLSE
   13    545-548 SPQE
   14    595-598 STFD

FIGURE 2A

```
        15    629-632  SIVD
        16    690-693  SPND
```

[4] PDOC00008 PS00008 MYRISTYL
N-myristoylation site

Number of matches: 3
```
        1    233-238  GATLAR
        2    309-314  GGPSST
        3    536-541  GLRMNS
```

[5] PDOC00009 PS00009 AMIDATION
Amidation site

Number of matches: 2
```
        1    91-94   KGRR
        2    427-430 KGKK
```

[6] PDOC00018 PS00018 EF_HAND
EF-hand calcium-binding domain

```
        178-190 DHSNNDRLEGAEI
```

BLAST Alignment to Top Hit:
```
>gi|2137061|pir||PC4183 1-phosphatidylinositol-4,5-bisphosphate
            phosphodiesterase  (EC 3.1.4.11) delta-1 - Chinese
            hamster (fragment)
 gb|AAA93481.1| (U50566) phospholipase C-delta1 [Cricetulus griseus]
            Length = 745

Score =  776 bits (1981), Expect = 0.0
 Identities = 382/746 (51%), Positives = 523/746 (69%), Gaps = 13/746 (1%)
 Frame = +3

Query: 147  GLTEDEDVRAMLRGSRLRKIRSRTWHKERLYRLQEDGLSWFQ-RRIPRAPSQHIFFVQH 323
            GL +D+D++A+L+GS+L K++S +W +ER Y+LQED  ++W + R++ R+P  +F ++
Sbjct: 1    GLQDDQDLQALLKGSQLLKVKSSSWRRERFYKLQEDCKTIWQESRKVMRSPESQLFSIED 60

Query: 324  IEAVREGHQSEGLRRFGGAFAPARCLTIAFKGRRKNLDLAAPTAEEAQRWVRGLTKLRAR 503
            I+ VR GH++EGL +F      RC +I FK +R   LDL AP++ +AQ WV+GL K+
Sbjct: 61   IQEVRMGHRTEGLEKFARDIPEDRCFSIVFKDQRNTLDLIAPSSADAQHWVQGLRKIIHH 120

Query: 504  LDAMSQRERLDHWIHSYLHRADSNQDSKMSFKEIKSLLRMVNVDMNDMYAYLLFKECDHS 683
            +M QR++L HWIHS L +AD N+D+KM+FKE+K   L+ +N+ ++D YA  +F+ECDHS
Sbjct: 121  SGSMDQRQKLQHWIHSCLRKADKNKDNKMNFKELKDFLKELNIQVDDSYARKIFRECDHS 180

Query: 684  NNDRLEGAEIEEFLRRLLKRPELEEIFHQYSGEDRVLSAPELLEFLE-DQGEEGATLARA 860
            D LE  EIE F + L +R E++  +F + +G    LS +L+ FL+  Q EE A  A A
Sbjct: 181  QTDSLEDEEIETFYKMLTQRAEIDRVFAEAAGSAETLSVEKLVTFLQHQQREEAAGPALA 240

Query: 861  QQLIQTYELNETAKQHELMTLDGFMMYLLSPEGTALDNTHTCVFQDMNQPLAHYFISSSH 1040
            LI+ YE +ETAK    MT DGF+MYLLS +G+A    H  V+QDM+QPL+HY +SSSH
Sbjct: 241  LSLIERYEPSETAKAQRQMTKDGFLMYLLSADGSAFSLAHRRVYQDMDQPLSHYLVSSSH 300
```

FIGURE 2B

```
Query: 1041  NTYLTDSQIGGPSSTEAYVRAFAQGCRCVELDCWEGPGGEPVIYHGHTLTSKILFRDVAQ 1220
              NTYL + Q+ GPSSTEAY+RA  +GCRC+ELDCW+GP  EP+IYHG+T TSKILF DV +
Sbjct: 301   NTYLLEDQLTGPSSTEAYIRALCKGCRCLELDCWDGPNQEPIIYHGYTFTSKILFYDVLR 360

Query: 1221  AVRDHAFTLSPYPVILSLENHCGLEQQAAMARHLCTILGDMLVTQALDSPNPEELPSPEQ 1400
              A+RD+AF  SPYPVILSLENHC LEQQ  MARHL   ILG ML+ Q LD     LPSPEQ
Sbjct: 361   AIRDYAFKASPYPVILSLENHCSLEQQQVMARHLKAILGPMLLDQPLDGVT-MSLPSPEQ 419

Query: 1401  LKGRVLVKGKK---LPAARSEDGRALSDREEGEEDDEEEEEEVEAAAQRRLAK---QISP 1562
              LKG++L+KGKK     L  A E+G  +D + +E  E E+E V +  Q++  +      ++P
Sbjct: 420   LKGKILLKGKKFGGLLPAGGENGPETTDVSDEDEAAEMEDEAVRSQVQQKSKEDKLNVAP 479

Query: 1563  ELSALAVYCHATRLRTL-HPAPNAPQPCQVSSLSERKAKKLIREAGNSFVRHNARQLTRV 1739
              ELS + +YC +       +P+ +        +++S SE +A +L++E+GN+FVRHN   L+R+
Sbjct: 480   ELSDMVIYCKSVHFGGFSNPSTSGQAFYEMASFSENRALRLLQESGNNFVRHNVSHLSRI 539

Query: 1740  YPLGLRMNSANYSPQEMMNSGCQLVALNFQTPGYEMDLNAGRFLVNGQCGYVLKPACLRQ 1919
              YP G R +S+NYSP EMWN GCQ+VALNFQTPG EMD+   GRF   NG CGYVLKPA LR
Sbjct: 540   YPAGRRTDSSNYSPVEMWNGGCQIVALNFQTPGPEMDVYLGRFQDNGACGYVLKPAFLRD 599

Query: 1920  PDSTFDP----EYPGPPRTTLSIQVLTAQQLPKLNAEKPHSIVDPLVRIEIHGVPADCAR 2087
              PD+  F+P     + P    + L ++V++ QQLPK+N  K  +SIVDP V +E+HGV  D A
Sbjct: 600   PDTAFNPRALTQGPWWAQKRLRVRVISGQQLPKVNKSK-NSIVDPKVIVEVHGVGQDVAS 658

Query: 2088  QETDYVLNNGFNPRWGQTLQFQLRAPELALVRFVVEDYDATSPNDFVGQFTLPLSSLKQG 2267
              ++T + NNGFNP W   +F++  P+LALVRFVVEDYDA+S NDF+GQ T+P +SLKQG
Sbjct: 659   RQTAVITNNGFNPWWDTEFEFEVAVPDLALVRFVVEDYDASSKNDFIGQSTIPWNSLKQG 718

Query: 2268  YRHIHLLSKDGASLSPATLFIQIRIQ 2345
              YRH+HLLSK+G      ATLF++I +Q
Sbjct: 719   YRHVHLLSKNGDQHPSATLFVKISLQ 744 (SEQ ID NO:4)

>gi|9790167|ref|NP_062650.1| phospholipase C, delta; PLC-delta 1;
          phospholipase C delta-1 [Mus musculus]
 gb|AAD00570.1| (U85711) phospholipase C delta-1; PI-PLC-delta-1 [Mus musculus]
 gb|AAD32616.1|AF133125_1 (AF133125) phospholipase C delta-1 [Mus musculus]
          Length = 756

Score =  761 bits (1943), Expect = 0.0
 Identities = 383/746 (51%), Positives = 512/746 (68%), Gaps = 13/746 (1%)
 Frame = +3

Query: 147   GLTEDEDVRAMLRGSRLRKIRSRTWHKERLYRLQEDGLSVWFQ-RRIPRAPSQHIFFVQH 323
              GL +D D++A+L+GS+L K++S +W +ER Y+LQED   +W + R++ R+P    +F ++
Sbjct: 12    GLQDDPDLQALLKGSQLLKVKSSSWRRERFYKLQEDCKTIWQESRKVMRSPESQLFSIED 71

Query: 324   IEAVREGHQSEGLRRFGGAFAPARCLTIAFKGRRKNLDLAAPTAEEAQRWVRGLTKLRAR 503
              I+ VR GH++EGL +F    RC +I FK +R  LDL AP+    + Q WV+GL K+  R
Sbjct: 72    IQEVRMGHRTEGLEKFARDIPEDRCFSIVFKDQRNTLDLIAPSPADVQHWVQGLRKIIDR 131
```

FIGURE 2C

```
Query:  504  LDAMSQRERLDHWIHSYLHRADSNQDSKMSFKEIKSLLRMVNVDMNDMYAYLLFKECDHS  683
             +M QR++L HWIHS L +AD N+D+KM+FKE+K  L+ +NV ++D YA  +F+ECDHS
Sbjct:  132  SGSMDQRQKLQHWIHSCLRKADKNKDNKMNFKEVKDFLKELNVQVDDSYARKIFRECDHS  191

Query:  684  NNDRLEGAEIEEFLRRLLKRPELEEIFHQYSGEDRVLSAPELLEFLE-DQGEEGATLARA  860
             D LE  EIE F R L +R E++  F + +G   LS  +L+ FL+  Q EE A  A A
Sbjct:  192  QTDSLEDEEIETFYRMLTQRAEIDRAFAEAAGSAETLSVEKLVTFLQHQQREEEAGPALA  251

Query:  861  QQLIQTYELNETAKQHELMTLDGFMMYLLSPEGTALDNTHTCVFQDMNQPLAHYFISSSH 1040
             LI+  YE +ETAK    MT DGF+MYLLS +G A    H  V+QDMNQPL+HY +SSSH
Sbjct:  252  LSLIERYEPSETAKAQRQMTKDGFLMYLLSADGNAFSLAHRRVYQDMNQPLSHYLVSSSH  311

Query: 1041  NTYLTDSQIGGPSSTEAYVRAFAQGCRCVELDCWEGPGGEPVIYHGHTLTSKILFRDVAQ 1220
             NTYL + Q+ GPSSTEAY+RA  +GCRC+ELDCW+GP   EP+IYHG+T TSKILF DV +
Sbjct:  312  NTYLLEDQLTGPSSTEAYIRALCKGCRCLELDCWDGPNQEPIIYHGYTFTSKILFCDVLR  371

Query: 1221  AVRDHAFTLSPYPVILSLENHCGLEQQAAMARHLCTILGDMLVTQALDSPNPEELPSPEQ 1400
             A+RD+AF  SPYPVILSLENHC LEQQ  MA HL  ILG ML+ Q LD       LPSPEQ
Sbjct:  372  AIRDYAFKASPYPVILSLENHCSLEQQRVMAHHLRAILGPMLLDQPLDGVT-TSLPSPEQ  430

Query: 1401  LKGRVLVKGKKLPA---ARSEDGRALSDREEGEEDDEEEEEEVEAAAQRRLAK---QISP 1562
             LK ++L+KGKKL     A  E+G    +D   +E   E E+EV +  Q +   + ++ P
Sbjct:  431  LKEKILLKGKKLGGLLPAGGENGPEATDVSDEDEAAEMEDEAVRSQVQHKPKEDKLKLVP  490

Query: 1563  ELSALAVYCHATRLRTL-HPAPNAPQPCQVSSLSERKAKKLIREAGNSFVRHNARQLTRV 1739
             ELS + +YC +        P+ +    +++S SE +A  +L++E+GNSFVRHN    L+R+
Sbjct:  491  ELSDMVIYCKSVHFGGFSSPSTSGQAFYEMASFSESRALRLLQESGNSFVRHNVGHLSRI  550

Query: 1740  YPLGLRMNSANYSPQEMWNSGCQLVALNFQTPGYEMDLNAGRFLVNGQCGYVLKPACLRQ 1919
             YP G R +S+NYSP EMWN GCQ+VALNFQTPG EMD+   G F  NG CGYVLKPA LR
Sbjct:  551  YPAGWRTDSSNYSPVEMWNGGCQIVALNFQTPGPEMDVYLGCFQDNGGCGYVLKPAFLRD  610

Query: 1920  PDSTFD----PEYPGPPRTTLSIQVLTAQQLPKLNAEKPHSIVDPLVRIEIHGVPADCAR 2087
             PD+TF+    + P   L +  +++  QQLPK+N  K +SIVDP V +EIHGV   D A
Sbjct:  611  PDTTFNSRALTQGPWWAPKKLRVWIISGQQLPKVNKNK-NSIVDPKVIVEIHGVGQDVAS  669

Query: 2088  QETDYVLNNGFNPRWGQTLQFQLRAPELALVRFVVEDYDATSPNDFVGQFTLPLSSLKQG 2267
             ++T +  NNGFNPRW    +F +   P+LALVRF+VEDYD++S NDF+GQ T+P +SLKQG
Sbjct:  670  RQTAVITNNGFNPRWDTEFEFVVAVPDLALVRFMVEDYDSSSKNDFIGQSTIPWNSLKQG  729

Query: 2268  YRHIHLLSKDGASLSPATLFIQIRIQ 2345
             YRH+HLLSK+G      ATLF++I IQ
Sbjct:  730  YRHVHLLSKNGDLHPSATLFVKISIQ  755  (SEQ ID NO:5)
```

Hmmer search results (Pfam):

| Model | Description | Score | E-value | N |
|---|---|---|---|---|
| PF00388 | Phosphatidylinositol-specific phospholipase | 258.0 | 1.2e-73 | 1 |
| PF00387 | Phosphatidylinositol-specific phospholipase | 190.6 | 2.4e-53 | 1 |
| PF00168 | C2 domain | 87.6 | 2e-22 | 1 |
| PF00169 | PH domain | 21.4 | 0.00014 | 1 |
| PF01023 | S-100/ICaBP type calcium binding domain | 7.3 | 2.3 | 1 |

FIGURE 2D

Parsed for domains:

| Model | Domain | seq-f | seq-t | hmm-f | hmm-t | score | E-value |
|---|---|---|---|---|---|---|---|
| PF00169 | 1/1 | 11 | 119 .. | 1 | 85 [] | 21.4 | 0.00014 |
| PF01023 | 1/1 | 203 | 229 .. | 8 | 37 .. | 7.3 | 2.3 |
| PF00388 | 1/1 | 285 | 430 .. | 1 | 153 [] | 258.0 | 1.2e-73 |
| PF00387 | 1/1 | 474 | 591 .. | 1 | 128 [] | 190.6 | 2.4e-53 |
| PF00168 | 1/1 | 609 | 699 .. | 1 | 95 [] | 87.6 | 2e-22 |

FIGURE 2E

```
   1 TTCCCCCAAC AGGTTCCTGG GGAGCTGAGG GTAAGGGGCC AGAAGTAGGG
  51 GCCCCCTCCA TTGGGAGCCT GCCCAAGTGG GGGCCCAGTC AGGCGTTCAG
 101 GCTGCCTGTG TTGATGGCCT GTTTGCAGAA GGCTCTGGAC AGAGCAGGCC
 151 CCGGTGACTC ACCCCCATTT CCGGCCTTAG TCACTCATCT CCCCCACACC
 201 CATGGGCTTG GCATCAGAGG GCTGGCCTAG GTAGGGGAGG CAGCCCCAGC
 251 TGCAGAGCCT GGTTGTCATG GCAATGAGCA GTCCCCCTTC CCATGGCCAA
 301 GGGGGTGTAG GAGGATGTGC CTAAGTGTAG TGGCGCTGCA GGCTCCCCTC
 351 TGCCCTCACC GTGTCATTGC TCAGGATGGG ACCATTTAGA GGCTACCTGG
 401 ACCTGGTGGG GGGGGGGGGT CTGGTGAGCC CCTCGGCCTG GCACGTGCCG
 451 TGTACACCCA GCTCTTTGTC TGGAAAGAGG AGGGTTCCAC TTTCCCCTTC
 501 CTGACCAGGG GGTACCGAGT GGGCATTCAC TCAGAGGGCC ACAGTCTAGA
 551 CCCTGAGGGA CCCTCTGGAG CTGTTAGGGC CACAGGCTGG CCCCAAGGGG
 601 TCATGGCCTC TTAAGGAGGT GGATTTCTCC TCTTGCCCCT GAGACCCTGA
 651 TTTTCAGTCA TGGTCAAAGT GGGTTTTAAA AATACAGATG CCCAGGCCCC
 701 ATCCCACACC AGCTGGGTGA GATGCCCTGG GCTGTGGTGT CTGCAGCCTC
 751 CCCTGGGTAA TTCCGATGCA CAGCTAAGGT TGAGAAACCC TGACCTGCGA
 801 GGCCTCTGCC CTGCGAGGCC TCTGCCCTGA ACTCTGGACA GATGGGGCAG
 851 AGCTGGGGAT AGAATTCACT TAGTCCCCCC ATCTGTCCGT CTACCTGTCT
 901 GCCCCTTCAG TCAACACTAG CTGGTATCCT GGCTCTGGGA TGAGCACTGT
 951 GGTGAGGAGA TAAGACCTCA TTCCGCCCTC AGATTTATTA AAGTATATAG
1001 GTGGGTTTTG TGTTTTATTT TAATTAAAGC AAAAAGTGCT GTTAGTGGTC
1051 AGAGAGGGAG AATGTCCACT TGAGGACAAA TCAAGGAAGG GTTCCTGGAG
1101 GAGGTGATAT CTGAACTGGT CCTTCAAGGA CTCAGATAGG AGGAAGAGAA
1151 GGGAGAAGGA TCCTACAAAA GGGTCCAAGA GAGGGTGAGA GGAGATGGTC
1201 CAGAGATATA GACTCAATTC CTTAGGTCAG AATTTGCAAT TGGGCAAGCC
1251 AGGGCCTTGG GGTCACAAAG CCAAACCCAG TATTAGGGGC TTGTCGAAAT
1301 AAAGGGAGGA AGAGAGGCCC TCTGTCTTAC TTCTTTTGGC CCACACAGGG
1351 GTTATTGATT TTTATTTTTT TTCAATTTGA TTTCGTTGTC AACATTAGAA
1401 TATCTGGAGG CTTCACACAC AGATCTATAT TCGGTTCTCT GGAAACTCCG
1451 GGCCCTCATT CACTCCGGGC TGTGCCCCAC CTCCAAAGGC CATGGACTCT
1501 CCGTTTACCC AGTTCCCACC TCCTCTATTG TCCTCTGACT CAAAAATCTT
1551 TGGTTGTGAC CTCGTTGAG GCATTGTAGA GCAGGGTGTG GCACTGTTTG
1601 GGCTGGGCAT CACGTGTTCC AGGGGGCCAG AGCCAGGAGA GGGCCGAAAC
1651 TCTCCGGGGC ACAGTGTCGG TCACGCTGTA GAAACCTCTG AATTTTGGAT
1701 TTTGCAGCAG GTATGATTGT GGTCTCCATT TTATGGATGG AGAACATGAG
1751 GCTTAGTGAC AGGTTAGTGC CACTGGGGCC ATGTATTAAA TAACTGGGAA
1801 GTGACAGTGT TGAGACTTAC TCCCCAGACT TCGGAATTCA GAAGCACTAG
1851 AAGAGCCGTG CAGTGCAGGG CCAAAGGTCA GAGGCGCTGG ACCCCGACCT
1901 CCAGAGCCCA AAGTGGCTTC TACCAGTATG GAATTCTGAC AACTTACTTA
1951 AGCTTCCCTG AGCCTCAGTT TCCTTGTCTG TTAGTACATG AGCAGGGCCT
2001 GCACACAGGA GATGCTTTTA TTTATTTATT TTTAGAGAC AGAGTCTCAC
2051 TCTGTTGCCC AAGCTGGAGT GCAGTGGCGC AATCTTGGCT CACTGCAACC
2101 TCCGCCTCCC GGATTCAAGT GATTCTCATG CCTCAGCCTC CCATGCCTGG
2151 AGATCAGCTG GCAGGGCTG ATCCTGGAGT CCTTGGCCTG TGACCCTGGA
2201 GCCAGGGTGG CCTCTGCTGT CCTCCTTGTC TTTGGGAAAG CAGAGGCAAG
2251 GTGCTTGGGT TACAGCAAGA GAGATCTAGG TTAGATGGTG AGACCTTCCT
2301 GATGGCTACG GTTTCACATC AAGGGAAAAA GGCTGTTGGT GGCAAATTCT
2351 GGACTTGAAG GCTGGAAGCC ATGTGGTGGG GGATAGTGGC AGAAAAGGCA
2401 ATTTTTTTTT TTTTTTGTTA AGACGCAGTC TCACTCTGTC GCTTAGGCTG
2451 CAGTGCAGTG GCACAATCTT GGCTCATGGC AACCTCAGCC TCCTAAGTAG
2501 CTGGGATTAC AGGCATGTGC CACCACACCC AGCTAATTTT GTATTTTTAG
2551 TAGAGGTGGG GTTGCACCAT GTTGGCCAGG CTGGTCTCGA ACTCCCGACC
2601 TCAAGTGATC CACCCACCTC GGCCTCCCAA GTGCTGAGAT TACAGGCGTG
2651 CAGCCGCGCC CTGCCAGAAA GGGAACCTTT AGTGAGGCCT GAGTCCCAGG
```

FIGURE 3A

```
2701 CATTGTCCGA GGGCAGTTCC ACACTGAGGG ACTGCAGAGG CCGCTGCTTG
2751 GAAGGAAGGA GGGAGATGGG GTACGGGTTG GGGGGCGCTT AGGGCTCCAA
2801 AGCCTAAAGC CAAACCCAGT GCAGGAGGCT TCTTACAATC GGGGAGGAGG
2851 GGAGTCCTGT GAGGGGAGG GAAGCTTACT GTGGGATGAA GGCCTGGGTT
2901 TGGAGAGGCT GGAGGATGGG GCAGCAGGTC CTATCGGGGG AGGGCAGGGG
2951 AGCCTCTGGG CAGGTACGGC CTGACGCCCC GGGTCCTCCC GCCCCGCCAG
3001 GCCTGACGGA GGACGAGGAC GTGCGCGCCA TGCTGCGGGG CTCCCGGCTC
3051 CGCAAGATCC GCTCGCGCAC GTGGCACAAG GAGCGGCTGT ACCGGCTGCA
3101 GGAGGACGGC CTGAGCGTGT GGTTCCAGCG GCGCATCCCG CGTGCGCCAT
3151 CGCAGCACAT CTGTGAGAGG CCGGGGAGCG CCGGGCGGAC AGGGAGGTGG
3201 GGACAGGCCC GGTCCTCCGC CCTGACCCGG CCCTCCTCTC AGTCTTCGTG
3251 CAGCACATCG AGGCGGTCCG CGAGGGCCAC CAGTCCGAGG GCCTGCGGCG
3301 CTTCGGGGGT GCCTTCGCGC CAGCGCGCTG CCTCACCATC GCCTTCAAGG
3351 GCCGCCGCAA GAACCTGGAC CTGGCGGCGC CCACGGCTGA GGAAGCGCAG
3401 CGCTGGGTGC GCGGTCTGAC CAAGCTCCGC GCGCGCCTGG ACGCCATGAG
3451 CCAGCGCGAG CGGCTAGACC AATATCCTGC CGGGGCTGGG AGGGAGGGCC
3501 CCATCCTTGG AGAGCCCTAA CCTTGGAGAG CCCCATCCTT GGAGAGCCCC
3551 CACGCCCAGG GAAGGCAGGG CCCCTGTCCT GAGGGCGCAC GGTCTGGGTC
3601 GGAGCCCTTG GTCTTCGAAA CTGAGGGTGG GGACACGCGC CCTGGCTAGG
3651 CCCAAGCTCC CACCAGGAGG GGTGGCGCGG CGCCTCCTTC AGGGAGGCCT
3701 GAGGCCTTCT GAGGGTGAAG ACAGGGCCTC CTGTCTTTGG TAAGCCCCAG
3751 TCCTGCGGAG GAGACACTGC TACCGTGCTC GGGGAGTGCA CAGGCCAAGG
3801 GGAAAGTACA GCCCCTAAAC TGGGGATCCC CCAGACCCAG GTGGGGGTGA
3851 CTTACCAGCC AGTTACCTGA GGGCTGGGGG CAGCCTGGCG TGTTGCTGTT
3901 ATTTCCTGAG CACCCACACC TGGATCCACT CCTATCTGCA CCGGGCTGAC
3951 TCCAACCAGG ACAGCAAGAT GAGCTTCAAG GAGATCAAGA GCCTGCTGAG
4001 AATGGTCAAC GTGGACATGA ACGACATGTA CGCCTACCTC CTCTTCAAGG
4051 TGGGCTTCCG CCCTGAACCC CAGCCCCTGG CTCTGCCATC ACTCTGACCT
4101 CTGCCTGCCC CCAGCCATCT GAATCATCAG CTCCCCTGCC CTCTCCATCT
4151 GCAGCTTTTT TGGAGCGAGC AGCCTTTCCC TGCACAAAGG CAACATCTGG
4201 GGTTAGTTAG CCTTTTGCCT CCCCTGAGGC CACTGGGCCA GGAAGGGAGT
4251 GGGGAGCCGG GGCCCAGAAC TTTCCTCATC CTCAGTTCCT ACCCCTCCAA
4301 AGTGAGCAGC AAAGCTGTTT TCATTTCCCT GAGTCTGCAA GGCACCTTTT
4351 GCACGTGGGG GCACAGGCAG GAGCCAGCCT ACAGGTGTGC ATGTGCACGG
4401 ATACACGTGT GCACCCTTCT CCACGCAGAC CCTCCACTGT GGCACGTGTT
4451 GGCACCTCAT GCATGGGAGC ACAGGGGCAC ACAGGAGTGG GCTCTGCAGC
4501 TATGGCCCAG CTGGAGCCCA TGGCAGACCT CTGTGTGCAT GTGGATGGTG
4551 GGACCCACCT GTGACCCCGA AAGACAGGAG AGCCCATGGC AGCTGGACCC
4601 CTGGGCCACA GCTTCACAGG GATGCTCCAT GAATTCTCAT TGACTTGTTC
4651 AATGACGCTG GGTGTGAATA TGTGCATGTC AGGATAGTAA CGTGTCCACC
4701 TAGGGGAGTG TGAGGGCCCA AGGGCCCTGT CTTGGCCCAG GGTCACCATT
4751 TTTCCTTCCA CATCTTGATT CCTGGGGTAG GTCATGGTGC AGAGGGGCAG
4801 GCACTGAACC AGAGAGACCT TTTAAGTCCA GCCCTGCCGG CCAGGCTCAG
4851 TGGCTCACCC CTGTCATCCC AGCACTTTGA GAGGCCTAGG CGGGAGGATT
4901 GCTTGAAGCC AGGAGTTTGA GATCAGCTTG GGCAACACAG CAAGACCCCA
4951 TCTCTACAAA AAATACAAAA ATTAGCCAGG TGCAGTGGTG CACACCAGTG
5001 GTCCCAGCTG TCCAGCTATT TGGAAGGCTG AGGTGGGAGG ATCACTTGAG
5051 ATCACGCGTT GGAAGCTGCA GTGAGCTATG ATCATGCCAC TGCGCTCCAG
5101 CCTGGGTAAC AGAGCAAGAC CAAACAAACA AACAAACCTA AAAAACAAAC
5151 CAAAAAGTCC TGCCCTGTAA TTTACCAGCT GTGTGAGCTA GAGTCACAAG
5201 TCTTACTCTG TTTTTCCACC TGTGAAATGG GGACCATTGC CTTCTCAGAT
5251 GTGGTAGATG ACAGATGGGT CAAAGGGGCC AGGTTTCCTG GAGTGTCTGG
5301 CTCCTCTGAG CTTCTCCTGC TGCTCCCAG GAGTGTGACC ACTCCAACAA
5351 CGACCGTCTA GAGGGGGCTG AGATCGAGGA GTTCCTGCGG CGGCTGCTGA
```

FIGURE 3B

```
5401 AGCGGCCGGA GCTGGAGGAG ATCTTCCATC AGTACTCGGG CGAGGACCGC
5451 GTGCTGAGTG CCCCTGAGCT GCTGGAGTTC CTGGAGGACC AGGGCGAGGA
5501 GGGCGCCACA CTGGCCCGCG CCCAGCAGCT CATTCAGACC TATGAGCTCA
5551 ACGAGACAGG TGGGGGGGGT GGCACGGCCA GGTCGTGGCA CCTGAAAGGG
5601 CTGTGTTCCC AGCTAAGCGG GTTCTGCTGC GGGCTGGCGC GGGCATCATC
5651 TCGGGCAGGT TACCTCACCT CCTCCAGACT CAGCTTCCAC ATGTGTAAAA
5701 TGGCACAACA GTTTGTCTTC CTCCCAGGGT CTGGTCGAAG GTTAAGTGGC
5751 ATGACTTACG TGGAGTCTAG TCAGTAGATT GTCTAGTCAT TATTCCTAAG
5801 CTGAGTGGGC CTTGGGGGCA TTGGAAGCTG GACATGGGGG ATCCCTATGT
5851 GGCCTGATGC CCTCTCCTGC CACCCCTGCA GCCAAGCAGC ATGAGCTGAT
5901 GACACTGGAT GGCTTCATGA TGTACCTGTT GTCGCCGGAG GGGGCTGCCT
5951 TGGACAACAC CCACACGTGT GTGTTCCAGG ACATGAACCA GCCCCTTGCC
6001 CACTACTTCA TCTCTTCCTC CCACAACACC TATCTGACTG ACTCCCAGAT
6051 CGGGGGGCCC AGCAGCACCG AGGCCTATGT TAGGTACTGT AGCAGGGGGT
6101 GAATGTTTCC GGGAGCCCCA CCTGGGGAGA GACATGGGCT GGCTTCCTGG
6151 GGCCTTCCTG GCCCAGCCTG CCTGCTGCCC TGCTCTGTGG CACTCTGGCA
6201 ACACCTTGCC CGTCCACCCA TCTGTCCACA CACAGGGCCT TTGCCCAGGG
6251 ATGCCGCTGC GTGGAGCTGG ACTGCTGGGA GGGGCCAGGA GGGGAGCCCG
6301 TCATCTATCA TGGCCATACC CTCACCTCCA AGATTCTCTT CCGGGACGTG
6351 GTCCAAGCCG TGCGCGACCA TGCCTTCACG GTGAGCCCCT GGGATGCCCA
6401 GCCCCAGCCC CACAGCCTTC CCAATGACCT CCGTCCGCAC TCACATGCCA
6451 GCTGCCCTCC GTCCTTCCAG AGGAAACCCT TGCCCAGAGA ATCATTCATT
6501 CACCAAGTGC TGCTGGGATA AGTGGCCAAT GGGGTGGCAT AAAGCTGAAT
6551 GAGATGCCAC CCTCATATTT GGGAAATATG TTCCCTCTCT CATATTTGGG
6601 AAATGTCCTA AAAATCACAG AGTTTCCAGA AGAAAACCTT TGGGGGAGGG
6651 AAGGACATTT TAATCATGAC TTCCAAAGAA TAAATAAGCT GTAAGAGAAG
6701 CTCACCAGTG GCATCTGCAT AAACACTGCA ACTTTGGTCA CAGTGTGCAA
6751 ATCTTCCCAT CAGCAAATGA TGGGAGGAGA GTTTTCACAT CACTGACATA
6801 GTCAATGTCA TTCACATGTA AAAAGCATTT ATGGGACCAG GTGCGGTGGC
6851 TCACACCCGT ATTCCCAGCA CTCTGGGAGG CTGACGCGAG GATCACTTGA
6901 GGCCAGGAAT TCCAGACCAG CCTGAGCAAA TAGCTACATC CTGTCTCAAC
6951 AAAAATAAAA ATTAGCTGAG TGTGGGGCA TGTGCCTGTA GGCTGAGTTA
7001 CTCAGGAGGC TGAGGTGGG GGATCACTTG AGCCCAGGAC TGGAGAACAC
7051 AGGGAGACTG ACTGTGCCAC TGCACTTCAG CCTGGGTGAT GGAGAGAGAC
7101 CAAAGCATAG ACAACAACAA CAAAAAATCG GCCAGGCGTG GTGGCTCTCA
7151 CCTGTAATCC CAGCACTTTG GGAGGCTGAG GTGGGCAGAT CACCTGAGGT
7201 CAGGAGTTTG AGACCAGCCT GGCCAACATG GTGAAACCTC ATCTCTATTA
7251 AAAATACAAA AATTAGCCGG GTGTGGTGGC GGGCGCCTGT AATCCCAGCT
7301 ACTTAGGAGG CTGAGGCAGG GAGAATCGCT TGAACCCGGG AGATGGAATT
7351 GTAGTGAGCT GAGATTGCAC CACTATACTC CAGCATGGGC GACAGAGCAA
7401 CACTCCATCT CAAAGAAAAA AAAAATAATT CCTGCAGCCG CCCTCAGCCT
7451 CCTGGACAGT CTGCTGCTTC CCTGGGTTCT CCAGAGCCCT GCCTTTGCCT
7501 GCCTGTCCTG AAGGGTCTGG GAGCCAGATG TTGGGAGATA CTGGCAGAGG
7551 GAGGGGAGTG GCTCTGAGCT GCTGCCCTTC CCCCCACAGC TGTCCCCTTA
7601 CCCTGTCATC CTATCCCTGG AGAACCACTG CGGGCTGGAG CAGCAGGCTG
7651 CCATGGCCCG CCACCTCTGC ACCATCCTGG GGACATGCT GGTGACACAG
7701 GCGCTGGACT CCCCAAATCC CGAGGAGCTG CCATCCCCAG AGGTGACGCC
7751 CCCCAGCCCC TAGTCTGGGT GGAGGGAGGT CTGGTGGGAG TCCGCCTCCC
7801 CGCACTGCTC GTGCCACCTC TGTGGCTCAG GACCCCTCAC CTCTTGCTGC
7851 CTTAACTTTT CTCTGTTCCT CTGTTCATCT GAGGTCTGCC ATCCCCTGGT
7901 CTTGTCCTTC TGCTGCCCTC TGGCTCTCCA TTCTTGACTA GACCCCCCCA
7951 CACACACACC CTCTTCTGTA ACCTGGCTTT GCCCTGCTGG CCCTGTGTCC
8001 CTGCCCGTAG AGTCCTGCAG GCTCTGCCAT TCCCACCTGC AAGGCCCCGC
8051 TTGACACTTT CTCCACCTGG AAGTCCCTTC TCGGCCATCC ACACTTGCCA
```

FIGURE 3C

```
8101 AGCGTCACCT GCTTAGAATT CAGCTCAACT TCAGCCGCCT CTTCCTGTGG
8151 CCTTATCCAC TTCCCCAACT CTCGGGCCTG AGGCGGCCTC CTGCTCTCCC
8201 CCAGACACCA GAGCGCGTCC TCGGCTCTCT CCAGACATTT ATCCTGTCGG
8251 GCTCCTTGAG AAAACTCTCC TCCTACTTCC AATCCCCAAC ATGCAGGCAG
8301 GGTTGACTCA CCCTCGTGTG TGTGTGAGAT GTGATTTTTG TTATTACTGT
8351 GAAAATCACA CCCGTATGGT AAAAGAAAAC TGAGCTGTAC TAAGGGACGC
8401 GATGAGCAGT GCTCCCCTCC CTCCACTGAC CTGTCCTCTT TCACAAGAAG
8451 TAACCATCTC TAACTTTCTT GCATGTCCTT CAAGAATTTC CCCACACACA
8501 TTACCTGTGT ACATATGTGT ACTGTCTTCT CTTTTAAATG GTACCAAAAA
8551 AGGACATGTG ATTCCAGGTT GTAGCCTCAC TTCTTCCACG TAAGATCTTC
8601 TTTGAAGAGG GTCCCTTTCC TTTCAGTCCT GAGCTGTCGC GTGCATTGTA
8651 GTGGCTGCTG TGTATATTCT GATGTTGAGG GACCTTATTA AGCATCCCTT
8701 CCTGATGGCC TCCCGGGCCA TTCTCCACTC TTTCCTATTA GAAACATCGC
8751 TCATCTCTGT GTCTCCTTTC CTGCCTCCCA CCCCTAGCCA GCCCCTCACA
8801 AGGCGGTGGT TGAATAACTG ACTGACTGGC TGCCACAGGG GCGAGAAGGC
8851 CTAACCCTTC ATCCTCCACG TTGGCCCCCA CAGCAGCTGA AGGGCCGGGT
8901 CCTGGTGAAG GGAAAGAAGC TGCCCGCTGC TCGGAGCGAG GATGGCCGGG
8951 CTCTGTCGGA TCGGGAGGAG GAGGAGGAGG ATGACGAGGA GGAAGAAGAG
9001 GAGGTGGAGG CTGCAGCGCA GAGGCGGCTG GTGAGAGCTG GGATGGGTGG
9051 GGTGGGGAAG GGGGGGAAGG TGGGAGGACG GATGTGGGAA GCGGGGCCCA
9101 GCTGAACCCC GCTGAGCCTG GTCTCCTAGG CCAAGCAGAT CTCCCCGGAG
9151 CTGTCGGCCC TGGCTGTGTA CTGCCACGCC ACCCGCCTGC GGACCCTGCA
9201 CCCTGCCCCC AACGCCCCAC AACCCTGCCA GGTCAGCTCC CTCAGCGAGC
9251 GCAAAGCCAA GAAACTCATT CGGGAGGCAG GTAGGAGCTG GGGCACTGGG
9301 TGTCTGGGGG CGAGAGGGTG AGAGACCTCC TGAAGGGAGT CTGGAAAGGA
9351 GTTGAGGGGG CTTTGGGGGA CAGTAAAGAG GTCAAGAGGA CCCCAAAGAG
9401 GGGCTGGGCT GAGGGAATGA GGGCCCCGCA CATGCCAGGG TGGATGGAGG
9451 GGAGTGGCAC GCTGAGGGCG GCCTGCTGTC TGCCTTCAGA GCCCTGTGGT
9501 GGGGCCGGCC ATAGAGGGTG ATGGGTCAGG CTGGGCTGGG GGCTGGGGGA
9551 GCCCAGCAGC TGCTGCAACA CTGGGGAGGA ATTCCTGGGG CAGGTGATGC
9601 TGAGAGGACA CATCACCTGG AGGACTAGGA AGCAGCCAGG TGAAGAGGGG
9651 AGAGCGCTTT CCAGACAGGA GGAACAGGTT GTTGAAGGCC TGGGGCCTTG
9701 GCCTGGAGAA GAATTCCAGG AACCACAGTG GAGCTGGAGG GCCGTGGGCA
9751 TTCAGTGTAC TTGGTTGGAA CTTTGTCAGG AGCTGGGAAT TGGGGGCTGG
9801 GGATGCAGGG CCAGGCTGTG TGGCTGGAGG GGGTCCCTGC AGCCTCCTCA
9851 GTGAGCTCCC CTCTCACTCT AGGTCAGAAG AGAGTGAGGA GCGGGGGCAG
9901 GGTGACCTGG GGACGGGCTT GGGCTCTGTT CCCTGGAGGT TACAGGCCGG
9951 GGCTTTGGGT GAGGGACCCC CGGAGTCTGT CACGGTCTCA CCCCAACTCT
10001 GCCCCAGGGA ACAGCTTTGT CAGGCACAAT GCCCGCCAGC TGACCCGCGT
10051 GTACCCGCTG GGGCTGCGGA TGAACTCAGC CAACTACAGT CCCCAGGAGA
10101 TGTGGAACTC GGGCTGTCAG CTGGGTAAGT GGGGGCCACA GGAATGAGAG
10151 CAGGCGGGGT GCCACAGTGT GGGGGAGGCC TCAGCAGTGA GGGGCCCACA
10201 CAGCCTTCCA GACGGTGGAA ACACGCATTT TGTTGATTAT TTTTAAAGTT
10251 GCCAGCAATG TAGGTGGGAA AATCAAATCA GGCTCGTTTG TTCTTGACAG
10301 TGTACAGGTC TCGCATTTTT ATCATGGTAG AAATTAAAAT CTCCACTCCC
10351 ATGTCCCCCG GACACACACA ACCCCCACAC ACCTGGCAGT CCCACTAAGT
10401 CAACACTGAC AAGGGTGGGC TCTGGGGGAC GCTGAGCCCC ACCAAAGGAG
10451 GGCTGTATCG TCTCCTTGGG GTAAGGATGG AAACCCCAGG CTTCCTCAGA
10501 CCCCTGGCTC TGACCCAAGC CTGGCCCTGA GGGTGGGGC TTTTTTAGTA
10551 CCTCCCACCC CAGTCTTGAG GGATCCCAGG GCAGAAGTAC AGGTGACAGT
10601 GGGGGCTGGG TCCATGACCC CCTCCCCTAA AGTCATGGTG GGAGCAGAGC
10651 AGCACTAAGC AGACAGTGGG ACCCCAGGCC CTTTGTAGAG AGGAATGCAG
10701 TCCCCTGAAA CTGAGTAGTG AGAACAGGGC CGCTAAGAGC CCCTGCTCTG
10751 ACCCTGCTGT GTCCACAGTG GCCTTGAACT TCCAGACGCC AGGCTACGAG
```

FIGURE 3D

```
10801 ATGGACCTCA ATGCCGGGCG CTTCCTAGTC AATGGGCAGT GTGGCTACGT
10851 CCTAAAACCT GCCTGCCTGC GGCAACCTGA CTCGACCTTT GACCCCGAGT
10901 ACCCAGGACC TCCCAGAACC ACTCTCAGCA TCCAGGTCAG CAGGCTGGAA
10951 CGGGCCCCAG TGTGGGGTCA GACTGGTTCT AGAAAGGCTC TTTGTGAGGT
11001 GGAGGAAGGC AAGGGAGGCT GGGGACATTT GGAAGTGAGG GTGGTGTGAG
11051 CTTGAGGCCC ATGAGGGGAT GGCCAAGGTG GGCGTGGGCC CCAGCCACTC
11101 CCTCCCTCAC CCACAGGTGC TGACTGCACA GCAGCTGCCC AAGCTGAATG
11151 CCGAGAAGCC ACACTCCATT GTGGACCCCC TGGTGCGCAT TGAGATCCAT
11201 GGGGTGCCCG CAGACTGTGC CCGGCAGGAG ACTGACTACG TGCTCAACAA
11251 TGGTGGGCAG CCACTGGCGG AAGTGGGGTT GGGGGAGACT GCAGAGAGCG
11301 AAGGGTGGTG CAGGGTGGGT CCTGGGGCCC CTGGGCTCTG ACTGCCATCC
11351 CTGTGCCCTA GGCTTCAACC CCCGCTGGGG GCAGACCCTG CAGTTCCAGC
11401 TGCGGGCTCC GGAGCTGGCA CTGGTCCGGT TTGTGGTGGA AGATTATGAC
11451 GCCACCTCCC CCAATGACTT TGTGGGCCAG TTTACACTGC CTCTTAGCAG
11501 CCTAAAGCAA GGTTGGTGGA GGCTGGTGGG GATGGAGAGG GATGTGGGTC
11551 CAGGTCCTGC AGACCCTGTT CACCTTTGTG CCTCGAATTT CCTGCCCTGA
11601 AGCAGGCCCG GGCTGGGCCA GACCCCCAGG GTGCACAGAG GACCTGAGGC
11651 CTGGCTGTCC TCCCTACAGG GTACCGCCAC ATACACCTGC TTTCCAAGGA
11701 CGGGGCCTCA CTGTCACCAG CCACGCTCTT CATCCAAATC CGCATCCAGC
11751 GCTCCTGAGG GCCCACCTCA CTCGCCTTGG GGTTCTGCGA GTGCCAGTCC
11801 ACATCCCCTG CAGAGCCCTC TCCTCCTCTG GAGTCAGGTG GTGGGAGTAC
11851 CAGCCCCCCA GCCCACCCAC TTGCCCACT CAGCCCATTC ACCAGGCGCT
11901 GGTCTCACCT GGGTGCTGAG GGCTGCCTGG GCCCCTCCTG AAGAACAGAA
11951 AGGTGTTCAT GTGACTTCAG TGAGCTCCAA CCCTGGGGCC CTGAGATGGC
12001 CCCAGCTCCT CTTGTCCTCA GCCCACCCCT CATTGTGACT TATGAGGAGC
12051 AAGCCTGTTG CTGCCAGGAG ACTTGGGGAG CAGGACACTT GTGGGCCCTC
12101 AGTTCCCCTC TGTCCTCCCG TGGGCCATCC CAGCCTCCTT CCCCCAGAGG
12151 AGCGCAGTCA CTCCACTTGG CCCCGACCCC GAGCTTAGCC CCTAAGCCCT
12201 CCTTTACCCC AGGCCTTCCT GGACTCCTCC CTCCAGCTCC GGAACCTGAG
12251 CTCCCCTTCC CTTCTCAAAG CAAGAAGGGA GCGCTGAGGC ATGAAGCCCT
12301 GGGGAAACTG GCAGTAGGTT TTGGTTTTTA TTTTTTGAGA CAGGGTCTCG
12351 CTCCGTCGCC CAGGCTGGAG TGCAATGTTG CAATCATGGC TCACTGCAGC
12401 TTTGAACTCC CAGGCTCAAG CGATCCTCCC ATCTCAGCCT CCTGAGTAGC
12451 TGGGACTACA GGCACAGGCC ACCAAACCTG GCTAATGTTT AAATTTTATG
12501 TAGAGATGGC GGGGGGGGCG GGGGTCTCCC TATGTTGCCC AGGCTGGTCT
12551 CGAGCTCCTG ACCTCAAGTG ATCCTCCTGC CCCAGCATTC CAAAGTGCTG
12601 GGATTACAGG TGTGAGCCAC TGCCTGGCCT GGCCGTAGGT TTGTAACTGT
12651 TTCATAGAAG AGCCCTGGAG AAGACAGTAG AATGAGCCTA TCTAGTTTAA
12701 AAAATAAAGA AGCACGTTGA TTTCACCACC GCCACTCCCT GAGCACCTCT
12751 ATGCTGCCAC CCCCACAGGC CCATGAGGAG GGACAGGGCT GGATGAGTTT
12801 CTTGGGCCTC TCCCCTCAAC AGGGCATGGA CTTGGCTAAG ACAGCCAGGG
12851 GGTGGCAGCA GGAGATGCCA CAGCTCTAAA TAGCCCGATC CCTGCTCCTG
12901 GCTTAAAGCT GCTGCGAGTA TCACAAGACT GTCTGAGGAT GCCAATTCAG
12951 CAGGTCAGCG CCTCCCCACA ACACACACAC ACACACACAC ACACACACAC
13001 TCACACATAC ACAGAGGGGC CTTGAATGAG GAGGAGACAG GAGTCTGAGG
13051 GACCCTCAGA CTGCCACTCT CCAGGCTTGG CTGGGCTCAA GGCCCCTGTC
13101 TGCTCAGTAG GGCAAATCCC AAGGACACGG GCTTCCCTTC CTCCAGCCAG
13151 CCAGCCTTTT ACACAAAGGC TGGAAACGCT GCTTGGGCCG CCTCTATAGA
13201 AATGCCAGGA GAGCGCACTG GACACTAGGC GACAGAATCT GGAGAAAATC
13251 CTGCACCCGC CCCTGCCAGC AGGGTGAAAT GTGGAGGCCT GGTGTTTTAG
13301 GTTCTGCCAG CCAACAGTGC CGGCACTGGA CAAGGGCAGA ACTTGACATT
13351 AGTCCCCAGA GGGTGGCCTG GAACTGGGCT GGGATAGGCC TTGAACTGGC
13401 CCCAAGCCCC ACAGAAACCA AACACAGGG CTGGGGCAGA CTCCACCTTC
13451 TAGCAACTCC AAGAACTAAT GCAGAAAGTG GCAGTGTCCC CCGCTCCTTC
```

FIGURE 3E

```
13501 ATGCTGGGAG TGGCGTTTGG CTCTGGTTAA TTTGTGTGTC TGAAAGAGGA
13551 TAATCAGAAT CAAAAGGGCC CAGAAGGAAT GGGCCGAGCC AGGCGGGCCG
13601 GGCCAGGCAG CCCGGGCATC TGGCCCTCAG GGCTGTCAGA GGGTCAGGCT
13651 GCCAAACTGC AGCCTCAGGA TGGGAGGCAC AGTGAGGCTA AGTCCAGTTT
13701 TAGCAAATGA AGAGCCATTA GCATTGCCCA GCCCCTGCAG AGCCAGGTCT
13751 GGCCAGGGGC TGGCTGGGGG GTCTGGGTCA GGTGAGCACC AGACCCAGGG
13801 CTGAGTGCCC ATCCTGCTTG GCTTCTCTGG TTTCGTATCT GGTACCAAGA
13851 GGAAGGGGTG AAGGCTAGGA TGAGGGCCCA ATACTGAGAA GGCTGCCTTG
13901 AAAGGGCAAG AGTCTTTTTT TTTTTTTCTT TTGAGACAAA GTCTTGCTCG
13951 TCC (SEQ ID NO:3)
```

FEATURES:
Start:    3000
Exon:     3000-3162
Intron:   3163-3242
Exon:     3243-3465
Intron:   3466-3910
Exon:     3911-4049
Intron:   4050-5330
Exon:     5331-5559
Intron:   5560-5881
Exon:     5882-6083
Intron:   6084-6235
Exon:     6236-6380
Intron:   6381-7589
Exon:     7590-7742
Intron:   7743-8883
Exon:     8884-9030
Intron:   9031-9129
Exon:     9130-9280
Intron:   9281-10007
Exon:     10008-10124
Intron:   10125-10768
Exon:     10769-10935
Intron:   10936-11116
Exon:     11117-11252
Intron:   11253-11361
Exon:     11362-11511
Intron:   11512-11669
Exon:     11670-11755
Stop:     11756

CHROMOSOME MAP POSITION:
Chromosome 17

ALLELIC VARIANTS (SNPs):

| DNA Position | Major | Minor | Domain | Protein Position | Major | Minor |
|---|---|---|---|---|---|---|
| 3242 | G | C | Intron | | | |
| 5158 | G | A T | Intron | | | |
| 5760 | G | A | Intron | | | |
| 5905 | C | T | Exon | 260 | L | L |
| 6536 | C | T G | Intron | | | |
| 6886 | G | T | Intron | | | |

FIGURE 3F

| | | | | | | | |
|---|---|---|---|---|---|---|---|
| 8920 | T | C | Exon | 431 | L | L | |
| 9060 | T | G | Intron | | | | |
| 10896 | C | T | Exon | 599 | P | P | |
| 12475 | C | A | Beyond ORF(3') | | | | |
| 12515 | - | G | Beyond ORF(3') | | | | |
| 12519 | - | G C | Beyond ORF(3') | | | | |
| 13000 | C | - | Beyond ORF(3') | | | | |
| 13625 | C | A | Beyond ORF(3') | | | | |
| 13919 | - | T | Beyond ORF(3') | | | | |
| 13924 | - | C T | Beyond ORF(3') | | | | |

Context:

DNA
Position

3242    GGGCAGGGGAGCCTCTGGGCAGGTACGGCCTGACGCCCCGGGTCCTCCCGCCCCGCCAGG
        CCTGACGGAGGACGAGGACGTGCGCGCCATGCTGCGGGGCTCCCGGCTCCGCAAGATCCG
        CTCGCGCACGTGGCACAAGGAGCGGCTGTACCGGCTGCAGGAGGACGGCCTGAGCGTGTG
        GTTCCAGCGGCGCATCCCGCGTGCGCCATCGCAGCACATCTGTGAGAGGCCGGGGAGCGC
        CGGGCGGACAGGGAGGTGGGGACAGGCCCGGTCCTCCGCCCTGACCCGGCCCTCCTCTCA
        [G,C]
        TCTTCGTGCAGCACATCGAGGCGGTCCGCGAGGGCCACCAGTCCGAGGGCCTGCGGCGCT
        TCGGGGGTGCCTTCGCGCCAGCGCGCTGCCTCACCATCGCCTTCAAGGGCCGCCGCAAGA
        ACCTGGACCTGGCGGCGCCCACGGCTGAGGAAGCGCAGCGCTGGGTGCGCGGTCTGACCA
        AGCTCCGCGCGCGCCTGGACGCCATGAGCCAGCGCGAGCGGCTAGACCAATATCCTGCCG
        GGGCTGGGAGGGAGGGCCCCATCCTTGGAGAGCCCTAACCTTGGAGAGCCCCATCCTTGG

5158    CCCCTGTCATCCCAGCACTTTGAGAGGCCTAGGCGGGAGGATTGCTTGAAGCCAGGAGTT
        TGAGATCAGCTTGGGCAACACAGCAAGACCCCATCTCTACAAAAAAATACAAAAATTAGCC
        AGGTGCAGTGGTGCACACCAGTGGTCCCAGCTGTCCAGCTATTTGGAAGGCTGAGGTGGG
        AGGATCACTTGAGATCACGCGTTGGAAGCTGCAGTGAGCTATGATCATGCCACTGCGCTC
        CAGCCTGGGTAACAGAGCAAGACCAAACAAACAAACAAACCTAAAAAACAAACCAAAAAG
        [G,A,T]
        CCTGCCCTGTAATTTACCAGCTGTGTGAGCTAGAGTCACAAGTCTTACTCTGTTTTTTCCA
        CCTGTGAAATGGGGACCATTGCCTTCTCAGATGTGGTAGATGACAGATGGGTCAAAGGGG
        CCAGGTTTCCTGGAGTGTCTGCCTCCTCTGAGCTTCTCCTGCTGCTCCCCAGGAGTGTGA
        CCACTCCAACAACGACCGTCTAGAGGGGCTGAGATCGAGGAGTTCCTGCGGCGGCTGCT
        GAAGCGGCCGGAGCTGGAGGAGATCTTCCATCAGTACTCGGGCGAGGACCGCGTGCTGAG

5760    GCCCCTGAGCTGCTGGAGTTCCTGGAGGACCAGGGCGAGGAGGGCGCCACACTGGCCCGC
        GCCCAGCAGCTCATTCAGACCTATGAGCTCAACGAGACAGGTGGGGGGGTGGCACGGCC
        AGGTCGTGGCACCTGAAAGGGCTGTGTTCCCAGCTAAGCGGGTTCTGCTGCGGGCTGGCG
        CGGGCATCATCTCGGGCAGGTTACCTCACCTCCTCCAGACTCAGCTTCCACATGTGTAAA
        ATGGCACAACAGTTTGTCTTCCTCCCAGGGTCTGGTCGAAGGTTAAGTGGCATGACTTAC
        [G,A]
        TGGAGTCTAGTCAGTAGATTGTCTAGTCATTATTCCTAAGCTGAGTGGGCCTTGGGGGCA
        TTGAAGCTGGACATGGGGGATCCCTATGTGGCCTGATGCCCTCTCCTGCCACCCCTGCA
        GCCAAGCAGCATGAGCTGATGACACTGGATGGCTTCATGATGTACCTGTTGTCGCCGGAG
        GGGGCTGCCTTGGACAACACCCACACGTGTGTGTTCCAGGACATGAACCAGCCCCTTGCC
        CACTACTTCATCTCTTCCTCCCACAACACCTATCTGACTGACTCCCAGATCGGGGGGCCC

5905    GTTCCCAGCTAAGCGGGTTCTGCTGCGGGCTGGCGCGGGCATCATCTCGGGCAGGTTACC
        TCACCTCCTCCAGACTCAGCTTCCACATGTGTAAAATGGCACAACAGTTTGTCTTCCTCC
        CAGGGTCTGGTCGAAGGTTAAGTGGCATGACTTACGTGGAGTCTAGTCAGTAGATTGTCT

FIGURE 3G

```
       AGTCATTATTCCTAAGCTGAGTGGGCCTTGGGGGCATTGGAAGCTGGACATGGGGGATCC
       CTATGTGGCCTGATGCCCTCTCCTGCCACCCCTGCAGCCAAGCAGCATGAGCTGATGACA
       [C,T]
       TGGATGGCTTCATGATGTACCTGTTGTCGCCGGAGGGGGCTGCCTTGGACAACACCCACA
       CGTGTGTGTTCCAGGACATGAACCAGCCCCTTGCCCACTACTTCATCTCTTCCTCCCACA
       ACACCTATCTGACTGACTCCCAGATCGGGGGGCCCAGCAGCACCGAGGCCTATGTTAGGT
       ACTGTAGCAGGGGGTGAATGTTTCCGGGAGCCCCACCTGGGGAGAGACATGGGCTGGCTT
       CCTGGGGCCTTCCTGGCCCAGCCTGCCTGCTGCCCTGCTCTGTGGCACTCTGGCAACACC
```

6536   GGCCTTTGCCCAGGGATGCCGCTGCGTGGAGCTGGACTGCTGGGAGGGGCCAGGAGGGGA
       GCCCGTCATCTATCATGGCCATACCCTCACCTCCAAGATTCTCTTCCGGGACGTGGTCCA
       AGCCGTGCGCGACCATGCCTTCACGGTGAGCCCCTGGGATGCCCAGCCCCAGCCCCACAG
       CCTTCCCAATGACCTCCGTCCGCACTCACATGCCAGCTGCCCTCCGTCCTTCCAGAGGAA
       ACCCTTGCCCAGAGAATCATTCATTCACCAAGTGCTGCTGGGATAAGTGGCCAATGGGGT
       [C,T,G]
       GCATAAAGCTGAATGAGATGCCACCCTCATATTTGGGAAATATGTTCCCTCTCTCATATT
       TGGGAAATGTCCTAAAAATCACAGAGTTTCCAGAAGAAAACCTTTGGGGGAGGGAAGGAC
       ATTTTTAATCATGACTTCCAAAGAATAAATAAGCTGTAAGAGAAGCTCACCAGTGGCATCT
       GCATAAACACTGCAACTTTGGTCACAGTGTGCAAATCTTCCCATCAGCAAATGATGGGAG
       GAGAGTTTTCACATCACTGACATAGTCAATGTCATTCACATGTAAAAAGCATTTATGGGA

6886   TCTCTCATATTTGGGAAATGTCCTAAAAATCACAGAGTTTCCAGAAGAAAACCTTTGGGG
       GAGGGAAGGACATTTTTAATCATGACTTCCAAAGAATAAATAAGCTGTAAGAGAAGCTCAC
       CAGTGGCATCTGCATAAACACTGCAACTTTGGTCACAGTGTGCAAATCTTCCCATCAGCA
       AATGATGGGAGGAGAGTTTTCACATCACTGACATAGTCAATGTCATTCACATGTAAAAAG
       CATTTATGGGACCAGGTGCGGTGGCTCACACCCGTATTCCCAGCACTCTGGGAGGCTGAC
       [G,T]
       CGAGGATCACTTGAGGCCAGGAATTCCAGACCAGCCTGAGCAAATAGCTACATCCTGTCT
       CAACAAAAATAAAAATTAGCTGAGTGTGGGGGCATGTGCCTGTAGGCTGAGTTACTCAGG
       AGGCTGAGGTGGGGGGATCACTTGAGCCCAGGACTGGAGAACACAGGGAGACTGACTGTG
       CCACTGCACTTCAGCCTGGGTGATGGAGAGAGACCAAAGCATAGACAACAACAACAAAAA
       ATCGGCCAGGCGTGGTGGCTCTCACCTGTAATCCCAGCACTTTGGGAGGCTGAGGTGGGC

8920   CTTTCAGTCCTGAGCTGTCGCGTGCATTGTAGTGGCTGCTGTGTATATTCTGATGTTGAG
       GGACCTTATTAAGCATCCCTTCCTGATGGCCTCCCGGGCCATTCTCCACTCTTTCCTATT
       AGAAACATCGCTCATCTCTGTGTCTCCTTTCCTGCCTCCCACCCCTAGCCAGCCCCTCAC
       AAGGCGGTGGTTGAATAACTGACTGACTGGCTGCCACAGGGGCGAGAAGGCCTAACCCTT
       CATCCTCCACGTTGGCCCCCACAGCAGCTGAAGGGCCGGGTCCTGGTGAAGGGAAAGAAG
       [T,C]
       TGCCCGCTGCTCGGAGCGAGGATGGCCGGGCTCTGTCGGATCGGGAGGAGGAGGAGGAGG
       ATGACGAGGAGGAAGAAGAGGAGGTGGAGGCTGCAGCGCAGAGGCGGCTGGTGAGAGCTG
       GGATGGGTGGGGTGGGGAAGGGGGGGAAGGTGGGAGGACGGATGTGGGAAGCGGGGCCCA
       GCTGAACCCCGCTGAGCCTGGTCTCCTAGGCCAAGCAGATCTCCCCGGAGCTGTCGGCCC
       TGGCTGTGTACTGCCACGCCACCCGCCTGCGGACCCTGCACCCTGCCCCCAACGCCCCAC

9060   TGTCTCCTTTCCTGCCTCCCACCCCTAGCCAGCCCCTCACAAGGCGGTGGTTGAATAACT
       GACTGACTGGCTGCCACAGGGGCGAGAAGGCCTAACCCTTCATCCTCCACGTTGGCCCCC
       ACAGCAGCTGAAGGGCCGGGTCCTGGTGAAGGGAAAGAAGCTGCCCGCTGCTCGGAGCGA
       GGATGGCCGGGCTCTGTCGGATCGGGAGGAGGAGGAGGAGGATGACGAGGAGGAAGAAGA
       GGAGGTGGAGGCTGCAGCGCAGAGGCGGCTGGTGAGAGCTGGGATGGGTGGGGTGGGGAA
       [T,G]
       GGGGGGAAGGTGGGAGGACGGATGTGGGAAGCGGGGCCCAGCTGAACCCCGCTGAGCCTG
       GTCTCCTAGGCCAAGCAGATCTCCCCGGAGCTGTCGGCCCTGGCTGTGTACTGCCACGCC
       ACCCGCCTGCGGACCCTGCACCCTGCCCCCAACGCCCCACAACCCTGCCAGGTCAGCTCC

FIGURE 3H

```
            CTCAGCGAGCGCAAAGCCAAGAAACTCATTCGGGAGGCAGGTAGGAGCTGGGGCACTGGG
            TGTCTGGGGGCGAGAGGGTGAGAGACCTCCTGAAGGGAGTCTGGAAAGGAGTTGAGGGGG

10896       AATGCCGGGCGCTTCCTAGTCAATGGGCAGTGTGGCTACGTCCTAAAACCTGCCTGCCTG
            CGGCAACCTGACTCGACCTTTGACCC
            [C,T]
            GAGTACCCAGGACCTCCCAGAACCACTCTCAGCATCCAGGTCAGCAGGCTGGAACGGGCC
            CCAGTGTGGGGTCAGACTGGTTCTAG

12475       GACCCCGAGCTTAGCCCCTAAGCCCTCCTTTACCCCAGGCCTTCCTGGACTCCTCCCTCC
            AGCTCCGGAACCTGAGCTCCCCTTCCCTTCTCAAAGCAAGAAGGGAGCGCTGAGGCATGA
            AGCCCTGGGGAAACTGGCAGTAGGTTTTGGTTTTTATTTTTTGAGACAGGGTCTCGCTCC
            GTCGCCCAGGCTGGAGTGCAATGTTGCAATCATGGCTCACTGCAGCTTTGAACTCCCAGG
            CTCAAGCGATCCTCCCATCTCAGCCTCCTGAGTAGCTGGGACTACAGGCACAGGCCACCA
            [C,A]
            ACCTGGCTAATGTTTAAATTTTATGTAGAGATGGCGGGGGGGGCGGGGGTCTCCCTATGT
            TGCCCAGGCTGGTCTCGAGCTCCTGACCTCAAGTGATCCTCCTGCCCCAGCATTCCAAAG
            TGCTGGGATTACAGGTGTGAGCCACTGCCTGGCCTGGCCGTAGGTTTGTAACTGTTTCAT
            AGAAGAGCCCTGGAGAAGACAGTAGAATGAGCCTATCTAGTTTAAAAAATAAAGAAGCAC
            GTTGATTTCACCACCGCCACTCCCTGAGCACCTCTATGCTGCCACCCCCACAGGCCCATG

12515       CTTCCTGGACTCCTCCCTCCAGCTCCGGAACCTGAGCTCCCCTTCCCTTCTCAAAGCAAG
            AAGGGAGCGCTGAGGCATGAAGCCCTGGGGAAACTGGCAGTAGGTTTTGGTTTTTATTTT
            TTGAGACAGGGTCTCGCTCCGTCGCCCAGGCTGGAGTGCAATGTTGCAATCATGGCTCAC
            TGCAGCTTTGAACTCCCAGGCTCAAGCGATCCTCCCATCTCAGCCTCCTGAGTAGCTGGG
            ACTACAGGCACAGGCCACCAAACCTGGCTAATGTTTAAATTTTATGTAGAGATGGCGGGG
            [-,G]
            GGGCGGGGGTCTCCCTATGTTGCCCAGGCTGGTCTCGAGCTCCTGACCTCAAGTGATCCT
            CCTGCCCCAGCATTCCAAAGTGCTGGGATTACAGGTGTGAGCCACTGCCTGGCCTGGCCG
            TAGGTTTGTAACTGTTTCATAGAAGAGCCCTGGAGAAGACAGTAGAATGAGCCTATCTAG
            TTTAAAAAATAAAGAAGCACGTTGATTTCACCACCGCCACTCCCTGAGCACCTCTATGCT
            GCCACCCCCACAGGCCCATGAGGAGGGACAGGGCTGGATGAGTTTCTTGGGCCTCTCCCC

12519       CTGGACTCCTCCCTCCAGCTCCGGAACCTGAGCTCCCCTTCCCTTCTCAAAGCAAGAAGG
            GAGCGCTGAGGCATGAAGCCCTGGGGAAACTGGCAGTAGGTTTTGGTTTTTATTTTTTGA
            GACAGGGTCTCGCTCCGTCGCCCAGGCTGGAGTGCAATGTTGCAATCATGGCTCACTGCA
            GCTTTGAACTCCCAGGCTCAAGCGATCCTCCCATCTCAGCCTCCTGAGTAGCTGGGACTA
            CAGGCACAGGCCACCAAACCTGGCTAATGTTTAAATTTTATGTAGAGATGGCGGGGGGGG
            [-,G,C]
            GGGGGTCTCCCTATGTTGCCCAGGCTGGTCTCGAGCTCCTGACCTCAAGTGATCCTCCTG
            CCCCAGCATTCCAAAGTGCTGGGATTACAGGTGTGAGCCACTGCCTGGCCTGGCCGTAGG
            TTTGTAACTGTTTCATAGAAGAGCCCTGGAGAAGACAGTAGAATGAGCCTATCTAGTTTA
            AAAAATAAAGAAGCACGTTGATTTCACCACCGCCACTCCCTGAGCACCTCTATGCTGCCA
            CCCCCACAGGCCCATGAGGAGGGACAGGGCTGGATGAGTTTCTTGGGCCTCTCCCCTCAA

13000       AAAAATAAAGAAGCACGTTGATTTCACCACCGCCACTCCCTGAGCACCTCTATGCTGCCA
            CCCCCACAGGCCCATGAGGAGGGACAGGGCTGGATGAGTTTCTTGGGCCTCTCCCCTCAA
            CAGGGCATGGACTTGGCTAAGACAGCCAGGGGGTGGCAGCAGGAGATGCCACAGCTCTAA
            ATAGCCCGATCCCTGCTCCTGGCTTAAAGCTGCTGCGAGTATCACAAGACTGTCTGAGGA
            TGCCAATTCAGCAGGTCAGCGCCTCCCCACAACACACACACACACACACACACACACACA
            [C,-]
            TCACACATACACAGAGGGGCCTTGAATGAGGAGGAGACAGGAGTCTGAGGGACCCTCAGA
            CTGCCACTCTCCAGGCTTGGCTGGGCTCAAGGCCCCTGTCTGCTCAGTAGGGCAAATCCC
            AAGGACACGGGCTTCCCTTCCTCCAGCCAGCCAGCCTTTTACACAAAGGCTGGAAACGCT
```

FIGURE 3I

```
              GCTTGGGCCGCCTCTATAGAAATGCCAGGAGAGCGCACTGGACACTAGGCGACAGAATCT
              GGAGAAAATCCTGCACCCGCCCCTGCCAGCAGGGTGAAATGTGGAGGCCTGGTGTTTTAG

13625     ACTGGACAAGGGCAGAACTTGACATTAGTCCCCAGAGGGTGGCCTGGAACTGGGCTGGGA
              TAGGCCTTGAACTGGCCCCAAGCCCCACAGAAACCAAAACACAGGGCTGGGGCAGACTCC
              ACCTTCTAGCAACTCCAAGAACTAATGCAGAAAGTGGCAGTGTCCCCCGCTCCTTCATGC
              TGGGAGTGGCGTTTGGCTCTGGTTAATTTGTGTGTCTGAAAGAGGATAATCAGAATCAAA
              AGGGCCCAGAAGGAATGGGCCGAGCCAGGCGGGCCGGGCCAGGCAGCCCGGGCATCTGGC
              [C,A]
              CTCAGGGCTGTCAGAGGGTCAGGCTGCCAAACTGCAGCCTCAGGATGGGAGGCACAGTGA
              GGCTAAGTCCAGTTTTAGCAAATGAAGAGCCATTAGCATTGCCCAGCCCCTGCAGAGCCA
              GGTCTGGCCAGGGGCTGGCTGGGGGGTCTGGGTCAGGTGAGCACCAGACCCAGGGCTGAG
              TGCCCATCCTGCTTGGCTTCTCTGGTTTCGTATCTGGTACCAAGAGGAAGGGGTGAAGGC
              TAGGATGAGGGCCCAATACTGAGAAGGCTGCCTTGAAAGGGCAAGAGTCTTTTTTTTTTT

13919     TCTGGCCCTCAGGGCTGTCAGAGGGTCAGGCTGCCAAACTGCAGCCTCAGGATGGGAGGC
              ACAGTGAGGCTAAGTCCAGTTTTAGCAAATGAAGAGCCATTAGCATTGCCCAGCCCCTGC
              AGAGCCAGGTCTGGCCAGGGGCTGGCTGGGGGGTCTGGGTCAGGTGAGCACCAGACCCAG
              GGCTGAGTGCCCATCCTGCTTGGCTTCTCTGGTTTCGTATCTGGTACCAAGAGGAAGGGG
              TGAAGGCTAGGATGAGGGCCCAATACTGAGAAGGCTGCCTTGAAAGGGCAAGAGTCTTTT
              [-,T]
              TTTTTTTTCTTTTGAGACAAAGTCTTGCTCGTCC

13924     CCCTCAGGGCTGTCAGAGGGTCAGGCTGCCAAACTGCAGCCTCAGGATGGGAGGCACAGT
              GAGGCTAAGTCCAGTTTTAGCAAATGAAGAGCCATTAGCATTGCCCAGCCCCTGCAGAGC
              CAGGTCTGGCCAGGGGCTGGCTGGGGGGTCTGGGTCAGGTGAGCACCAGACCCAGGGCTG
              AGTGCCCATCCTGCTTGGCTTCTCTGGTTTCGTATCTGGTACCAAGAGGAAGGGGTGAAG
              GCTAGGATGAGGGCCCAATACTGAGAAGGCTGCCTTGAAAGGGCAAGAGTCTTTTTTTTT
              [-,C,T]
              TTTCTTTTGAGACAAAGTCTTGCTCGTCC
```

FIGURE 3J

SEQUENCE LISTING

<160> NUMBER OF SEQ ID NOS: 5

<210> SEQ ID NO 1
<211> LENGTH: 2211
<212> TYPE: PRT
<213> ORGANISM: Human

<400> SEQUENCE: 1

```
Ala Thr Gly Gly Gly Cys Cys Thr Gly Ala C ys Gly Gly Ala Gly Gly
 1               5                   10                  15

Ala Cys Gly Ala Gly Gly Ala Cys Gly Thr G ly Cys Gly Cys Gly Cys
                20                  25                  30

Cys Ala Thr Gly Cys Thr Gly Cys Gly Gly G ly Gly Cys Thr Cys Cys
        35                  40                  45
```

-continued

```
Cys Gly Gly Cys Thr Cys Cys Gly Cys Ala A la Gly Ala Thr Cys Cys
    50                  55                  60

Gly Cys Thr Cys Gly Cys Gly Cys Ala Cys G ly Thr Gly Gly Cys Ala
65                  70                  75                  80

Cys Ala Ala Gly Gly Ala Gly Cys Gly Gly C ys Thr Gly Thr Ala Cys
                85                  90                  95

Cys Gly Gly Cys Thr Gly Cys Ala Gly Gly A la Gly Gly Ala Cys Gly
            100                 105                 110

Gly Cys Cys Thr Gly Ala Gly Cys Gly Thr G ly Thr Gly Gly Thr Thr
        115                 120                 125

Cys Cys Ala Gly Cys Gly Gly Cys Gly Cys A la Thr Cys Cys Cys Gly
    130                 135                 140

Cys Gly Thr Gly Cys Gly Cys Cys Ala Thr C ys Gly Cys Ala Gly Cys
145                 150                 155                 160

Ala Cys Ala Thr Cys Thr Thr Cys Thr Thr C ys Gly Thr Gly Cys Ala
                165                 170                 175

Gly Cys Ala Cys Ala Thr Cys Gly Ala Gly G ly Cys Gly Gly Thr Cys
            180                 185                 190

Cys Gly Cys Gly Ala Gly Gly Gly Cys Cys A la Cys Cys Ala Gly Thr
        195                 200                 205

Cys Cys Gly Ala Gly Gly Gly Cys Cys Thr G ly Cys Gly Gly Cys Gly
    210                 215                 220

Cys Thr Thr Cys Gly Gly Gly Gly Gly Thr G ly Cys Cys Thr Thr Cys
225                 230                 235                 240

Gly Cys Gly Cys Cys Ala Gly Cys Gly Cys G ly Cys Thr Gly Cys Cys
                245                 250                 255

Thr Cys Ala Cys Cys Ala Thr Cys Gly Cys C ys Thr Thr Cys Ala Ala
            260                 265                 270

Gly Gly Gly Cys Cys Gly Cys Cys Gly Cys A la Ala Gly Ala Ala Cys
        275                 280                 285

Cys Thr Gly Gly Ala Cys Cys Thr Gly Gly C ys Gly Gly Cys Gly Cys
    290                 295                 300

Cys Cys Ala Cys Gly Gly Cys Thr Gly Ala G ly Gly Ala Ala Gly Cys
305                 310                 315                 320

Gly Cys Ala Gly Cys Gly Cys Thr Gly Gly G ly Thr Gly Cys Gly Cys
                325                 330                 335

Gly Gly Thr Cys Thr Gly Ala Cys Cys Ala A la Gly Cys Thr Cys Cys
            340                 345                 350

Gly Cys Gly Cys Gly Cys Gly Cys Cys Thr G ly Gly Ala Cys Gly Cys
        355                 360                 365

Cys Ala Thr Gly Ala Gly Cys Cys Ala Gly C ys Gly Cys Gly Ala Gly
    370                 375                 380

Cys Gly Gly Cys Thr Ala Gly Ala Cys Cys A la Cys Thr Gly Gly Ala
385                 390                 395                 400

Thr Cys Cys Ala Cys Thr Cys Cys Thr Ala T hr Cys Thr Gly Cys Ala
                405                 410                 415

Cys Cys Gly Gly Gly Cys Thr Gly Ala Cys T hr Cys Cys Ala Ala Cys
            420                 425                 430

Cys Ala Gly Gly Ala Cys Ala Gly Cys Ala A la Gly Ala Thr Gly Ala
        435                 440                 445

Gly Cys Thr Thr Cys Ala Ala Gly Gly Ala G ly Ala Thr Cys Ala Ala
    450                 455                 460
```

```
Gly Ala Gly Cys Cys Thr Gly Cys Thr Gly Ala Gly Ala Ala Thr Gly
465                 470                 475                 480
Gly Thr Cys Ala Ala Cys Gly Thr Gly Gly Ala Cys Ala Thr Gly Ala
            485                 490                 495
Ala Cys Gly Ala Cys Ala Thr Gly Thr Ala Cys Gly Cys Cys Thr Ala
            500                 505                 510
Cys Cys Thr Cys Thr Cys Thr Thr Cys Ala Ala Gly Gly Ala Gly Gly
        515                 520                 525
Thr Gly Thr Gly Ala Cys Cys Ala Cys Cys Cys Ala Ala Cys Ala
    530                 535                 540
Ala Cys Gly Ala Cys Cys Gly Thr Cys Thr Ala Gly Ala Gly Gly Gly
545                 550                 555                 560
Gly Gly Cys Thr Gly Ala Gly Ala Thr Cys Gly Ala Gly Gly Ala Gly
            565                 570                 575
Thr Thr Cys Cys Thr Gly Cys Gly Gly Cys Gly Gly Cys Thr Gly Cys
            580                 585                 590
Thr Gly Ala Ala Gly Cys Gly Gly Cys Gly Gly Ala Gly Cys Thr
    595                 600                 605
Gly Gly Ala Gly Gly Ala Gly Ala Thr Cys Thr hr Thr Cys Ala Thr
            610                 615                 620
Cys Ala Gly Thr Ala Cys Thr Cys Gly Gly Gly Cys Gly Ala Gly Gly
625                 630                 635                 640
Ala Cys Cys Gly Cys Gly Thr Gly Cys Thr Gly Ala Gly Thr Gly Cys
            645                 650                 655
Cys Cys Cys Thr Gly Ala Gly Cys Thr Gly Cys Thr Gly Gly Ala Gly
            660                 665                 670
Thr Thr Cys Cys Thr Gly Gly Ala Gly Gly Ala Cys Cys Ala Gly Gly
        675                 680                 685
Gly Cys Gly Ala Gly Gly Ala Gly Gly Gly Cys Gly Cys Cys Ala Cys
690                 695                 700
Ala Cys Thr Gly Gly Cys Cys Cys Gly Cys Gly Cys Cys Ala Gly
705                 710                 715                 720
Cys Ala Gly Cys Thr Cys Ala Thr Thr Cys Ala Gly Ala Cys Cys Thr
            725                 730                 735
Ala Thr Gly Ala Gly Cys Thr Cys Ala Ala Cys Gly Ala Gly Ala Cys
            740                 745                 750
Ala Gly Cys Cys Ala Ala Gly Cys Ala Gly Cys Ala Thr Gly Ala Gly
        755                 760                 765
Cys Thr Gly Ala Thr Gly Ala Cys Ala Cys Thr Gly Gly Ala Thr Gly
    770                 775                 780
Gly Cys Thr Thr Cys Ala Thr Gly Ala Thr Gly Thr Ala Cys Cys Thr
785                 790                 795                 800
Gly Thr Thr Gly Thr Cys Gly Cys Gly Gly Ala Gly Gly Gly Gly
            805                 810                 815
Ala Cys Thr Gly Cys Cys Thr Gly Gly Ala Cys Ala Ala Cys Ala
            820                 825                 830
Cys Cys Cys Ala Cys Ala Cys Gly Thr Gly Thr Gly Thr Gly Thr Thr
        835                 840                 845
Cys Cys Ala Gly Gly Ala Cys Ala Thr Gly Ala Ala Cys Cys Ala Gly
        850                 855                 860
Cys Cys Cys Cys Thr Thr Gly Cys Cys Ala Cys Thr Ala Cys Thr
865                 870                 875                 880
Thr Cys Ala Thr Cys Thr Cys Thr Thr Cys Cys Thr Cys Cys Cys Ala
```

-continued

```
                885                 890                 895
Cys Ala Ala Cys Ala Cys Cys Thr Ala Thr Cys Thr Gly Ala Cys Thr
            900                 905                 910
Gly Ala Cys Thr Cys Cys Ala Gly Ala Thr Cys Gly Gly Gly Gly
        915                 920                 925
Gly Gly Cys Cys Ala Gly Cys Ala Gly Cys Ala Cys Cys Gly Ala
    930                 935                 940
Gly Gly Cys Cys Thr Ala Thr Gly Thr Thr Ala Gly Gly Cys Cys
945                 950                 955                 960
Thr Thr Thr Gly Cys Cys Ala Gly Gly Ala Thr Gly Cys Cys
                965                 970                 975
Gly Cys Thr Gly Cys Gly Thr Gly Gly Ala Gly Cys Thr Gly Ala
            980                 985                 990
Cys Thr Gly Cys Thr Gly Gly Ala Gly Gly Gly Cys Cys Ala
        995                 1000                1005
Gly Gly Ala Gly Gly Gly Ala Gly Cys Cys Gly Thr Cys Ala
    1010                1015                1020
Thr Cys Thr Ala Thr Cys Ala Thr Gly Gly Cys Cys Ala Thr Ala Cys
1025                103 0                1035                1040
Cys Cys Thr Cys Ala Cys Cys Thr Cys Cys Ala Ala Gly Ala Thr Thr
                1045                1050                1055
Cys Thr Cys Thr Thr Cys Gly Gly Ala Cys Gly Thr Gly Gly
            1060                1065                1070
Cys Cys Cys Ala Ala Gly Cys Cys Gly Thr Gly Cys Gly Cys Gly Ala
        1075                1080                1085
Cys Cys Ala Thr Gly Cys Thr Thr Cys Ala Cys Gly Cys Thr Gly
    1090                1095                1100
Thr Cys Cys Cys Cys Thr Thr Ala Cys Cys Cys Thr Gly Thr Cys Ala
1105                111 0                1115                1120
Thr Cys Cys Thr Ala Thr Cys Cys Cys Thr Gly Gly Ala Gly Ala Ala
                1125                1130                1135
Cys Cys Ala Cys Thr Gly Cys Gly Gly Gly Cys Thr Gly Gly Ala Gly
        1140                1145                1150
Cys Ala Gly Cys Ala Gly Gly Cys Thr Gly Cys Cys Ala Thr Gly Gly
    1155                1160                1165
Cys Cys Cys Gly Cys Cys Ala Cys Cys Thr Cys Thr Gly Cys Ala Cys
    1170                1175                1180
Cys Ala Thr Cys Cys Thr Gly Gly Gly Gly Gly Ala Cys Ala Thr Gly
1185                119 0                1195                1200
Cys Thr Gly Gly Thr Gly Ala Cys Ala Cys Ala Gly Gly Cys Gly Cys
        1205                1210                1215
Thr Gly Gly Ala Cys Thr Cys Cys Cys Ala Ala Thr Cys Cys
    1220                1225                1230
Cys Gly Ala Gly Gly Ala Gly Cys Thr Gly Cys Cys Ala Thr Cys Cys
        1235                1240                1245
Cys Cys Ala Gly Ala Gly Cys Ala Gly Cys Thr Gly Ala Ala Gly Gly
    1250                1255                1260
Gly Cys Cys Gly Gly Gly Thr Cys Cys Thr Gly Gly Thr Gly Ala Ala
1265                127 0                1275                1280
Gly Gly Gly Ala Ala Ala Gly Ala Ala Gly Cys Thr Gly Cys Cys Cys
                1285                1290                1295
Gly Cys Thr Gly Cys Thr Cys Gly Gly Ala Gly Cys Gly Ala Gly Gly
            1300                1305                1310
```

```
Ala Thr Gly Gly Cys Cys Gly Gly Gly Cys T hr Cys Thr Gly Thr Cys
        1315                1320                1325

Gly Gly Ala Thr Cys Gly Gly Gly Ala Gly G ly Ala Gly Gly Gly Gly
        1330                1335                1340

Gly Ala Gly Gly Ala Gly Gly Ala Thr Gly A la Cys Gly Ala Gly Gly
1345                135 0                1355                1360

Ala Gly Gly Ala Ala Gly Ala Ala Gly Ala G ly Gly Ala Gly Gly Thr
        1365                1370                1375

Gly Gly Ala Gly Gly Cys Thr Gly Cys Ala G ly Cys Gly Cys Ala Gly
        1380                1385                1390

Ala Gly Gly Cys Gly Gly Cys Thr Gly Gly C ys Cys Ala Ala Gly Cys
        1395                1400                1405

Ala Gly Ala Thr Cys Thr Cys Cys Cys G ly Gly Ala Gly Cys Thr
        1410                1415                1420

Gly Thr Cys Gly Gly Cys Cys Cys Thr Gly G ly Cys Thr Gly Thr Gly
1425                143 0                1435                1440

Thr Ala Cys Thr Gly Cys Cys Ala Cys Gly C ys Cys Ala Cys Cys Cys
        1445                1450                1455

Gly Cys Cys Thr Gly Cys Gly Gly Ala Cys C ys Cys Thr Gly Cys Ala
        1460                1465                1470

Cys Cys Cys Thr Gly Cys Cys Cys Cys A la Ala Cys Gly Cys Cys
        1475                1480                1485

Cys Cys Ala Cys Ala Ala Cys Cys Thr G ly Cys Cys Ala Gly Gly
        1490                1495                1500

Thr Cys Ala Gly Cys Thr Cys Cys Thr C ys Ala Gly Cys Gly Ala
1505                151 0                1515                1520

Gly Cys Gly Cys Ala Ala Ala Gly Cys Cys A la Ala Gly Ala Ala Ala
        1525                1530                1535

Cys Thr Cys Ala Thr Thr Cys Gly Gly Gly A la Gly Gly Cys Ala Gly
        1540                1545                1550

Gly Gly Ala Ala Cys Ala Gly Cys Thr Thr T hr Gly Thr Cys Ala Gly
        1555                1560                1565

Gly Cys Ala Cys Ala Ala Thr Gly Cys Cys C ys Gly Cys Cys Ala Gly
        1570                1575                1580

Cys Thr Gly Ala Cys Cys Cys Gly Cys T hr Gly Thr Ala Cys Cys
1585                159 0                1595                1600

Cys Gly Cys Thr Gly Gly Gly Gly Cys Thr G ly Cys Gly Gly Ala Thr
        1605                1610                1615

Gly Ala Ala Cys Thr Cys Ala Gly Cys Cys A la Ala Cys Thr Ala Cys
        1620                1625                1630

Ala Gly Thr Cys Cys Cys Ala Gly Gly A la Gly Ala Thr Gly Thr
        1635                1640                1645

Gly Gly Ala Ala Cys Thr Cys Gly Gly Gly C ys Thr Gly Thr Cys Ala
        1650                1655                1660

Gly Cys Thr Gly Gly Thr Gly Cys Cys T hr Thr Gly Ala Ala Cys
1665                167 0                1675                1680

Thr Thr Cys Cys Ala Gly Ala Cys Gly Cys C ys Ala Gly Gly Cys Thr
        1685                1690                1695

Ala Cys Gly Ala Gly Ala Thr Gly Gly Ala C ys Cys Thr Cys Ala Ala
        1700                1705                1710

Thr Gly Cys Cys Gly Gly Gly Cys Gly Cys T hr Thr Cys Cys Thr Ala
        1715                1720                1725
```

-continued

Gly Thr Cys Ala Ala Thr Gly Gly Cys Ala Gly Thr Gly Thr Gly
    1730                1735                1740

Gly Cys Thr Ala Cys Gly Thr Cys Cys Thr Ala Ala Ala Cys Cys
1745                1750                1755                1760

Thr Gly Cys Cys Thr Gly Cys Cys Thr Gly Cys Gly Gly Cys Ala Ala
            1765                1770                1775

Cys Cys Thr Gly Ala Cys Thr Cys Gly Ala Cys Cys Thr Thr Thr Gly
            1780                1785                1790

Ala Cys Cys Cys Gly Ala Gly Thr Ala Cys Cys Cys Ala Gly Gly
        1795                1800                1805

Ala Cys Cys Thr Cys Cys Cys Ala Gly Ala Ala Cys Cys Ala Cys Thr
        1810                1815                1820

Cys Thr Cys Ala Gly Cys Ala Thr Cys Cys Ala Gly Gly Thr Gly Cys
1825                1830                1835                1840

Thr Gly Ala Cys Thr Gly Cys Ala Cys Ala Gly Cys Ala Gly Cys Thr
            1845                1850                1855

Gly Cys Cys Cys Ala Ala Gly Cys Thr Gly Ala Ala Thr Gly Cys Cys
            1860                1865                1870

Gly Ala Gly Ala Ala Gly Cys Cys Ala Cys Ala Cys Thr Cys Cys Ala
        1875                1880                1885

Thr Thr Gly Thr Gly Gly Ala Cys Cys Cys Cys Thr Gly Gly Thr
        1890                1895                1900

Gly Cys Gly Cys Ala Thr Thr Gly Ala Gly Ala Thr Cys Cys Ala Thr
1905                1910                1915                1920

Gly Gly Gly Gly Thr Gly Cys Cys Cys Gly Cys Ala Gly Ala Cys Thr
            1925                1930                1935

Gly Thr Gly Cys Cys Cys Gly Gly Cys Ala Gly Gly Ala Gly Ala Cys
            1940                1945                1950

Thr Gly Ala Cys Thr Ala Cys Gly Thr Gly Cys Thr Cys Ala Ala Cys
        1955                1960                1965

Ala Ala Thr Gly Gly Cys Thr Thr Cys Ala Ala Cys Cys Cys Cys
        1970                1975                1980

Gly Cys Thr Gly Gly Gly Gly Cys Ala Gly Ala Cys Cys Cys Thr
1985                1990                1995                2000

Gly Cys Ala Gly Thr Thr Cys Cys Ala Gly Cys Thr Gly Cys Gly Gly
            2005                2010                2015

Gly Cys Thr Cys Cys Gly Gly Ala Gly Cys Thr Gly Gly Cys Ala Cys
            2020                2025                2030

Thr Gly Gly Thr Cys Cys Gly Gly Thr Thr Thr Gly Thr Gly Gly Thr
            2035                2040                2045

Gly Gly Ala Ala Gly Ala Thr Thr Ala Thr Gly Ala Cys Gly Cys Cys
        2050                2055                2060

Ala Cys Cys Thr Cys Cys Cys Cys Ala Ala Thr Gly Ala Cys Thr
2065                2070                2075                2080

Thr Thr Gly Thr Gly Gly Gly Cys Cys Ala Gly Thr Thr Ala Cys
            2085                2090                2095

Ala Cys Thr Gly Cys Cys Thr Cys Thr Thr Ala Gly Cys Ala Gly Cys
        2100                2105                2110

Cys Thr Ala Ala Ala Gly Cys Ala Ala Gly G ly Gly Thr Ala Cys Cys
2115 2120 2125

Gly Cys Cys Ala Cys Ala Thr Ala Cys Ala C ys Cys Thr Gly Cys Thr
2130 2135 2140

Thr Thr Cys Cys Ala Ala Gly Gly Ala Cys G ly Gly Gly Gly Cys Cys

```
                 2145              215 0             2155              2160
       Thr Cys Ala Cys Thr Gly Thr Cys Ala Cys C ys Ala Gly Cys Cys Ala
                     2165              2170              2175
       Cys Gly Cys Thr Cys Thr Thr Cys Ala Thr C ys Cys Ala Ala Ala Thr
                     2180              2185              2190
       Cys Cys Gly Cys Ala Thr Cys Cys Ala Gly C ys Gly Cys Thr Cys Cys
                 2195              2200              2205
       Thr Gly Ala
           2210

<210> SEQ ID NO 2
<211> LENGTH: 736
<212> TYPE: PRT
<213> ORGANISM: Human

<400> SEQUENCE: 2

Met Gly Leu Thr Glu Asp Glu Val Arg A la Met Leu Arg Gly Ser
  1               5                  10                  15

Arg Leu Arg Lys Ile Arg Ser Arg Thr Trp H is Lys Glu Arg Leu Tyr
                 20                  25                  30

Arg Leu Gln Glu Asp Gly Leu Ser Val Trp P he Gln Arg Arg Ile Pro
             35                  40                  45

Arg Ala Pro Ser Gln His Ile Phe Phe Val G ln His Ile Glu Ala Val
         50                  55                  60

Arg Glu Gly His Gln Ser Glu Gly Leu Arg A rg Phe Gly Gly Ala Phe
 65                  70                  75                  80

Ala Pro Ala Arg Cys Leu Thr Ile Ala Phe L ys Gly Arg Arg Lys Asn
                 85                  90                  95

Leu Asp Leu Ala Ala Pro Thr Ala Glu Glu A la Gln Arg Trp Val Arg
                100                 105                 110

Gly Leu Thr Lys Leu Arg Ala Arg Leu Asp A la Met Ser Gln Arg Glu
            115                 120                 125

Arg Leu Asp His Trp Ile His Ser Tyr Leu H is Arg Ala Asp Ser Asn
        130                 135                 140

Gln Asp Ser Lys Met Ser Phe Lys Glu Ile L ys Ser Leu Leu Arg Met
145                 150                 155                 160

Val Asn Val Asp Met Asn Asp Met Tyr Ala T yr Leu Leu Phe Lys Glu
                165                 170                 175

Cys Asp His Ser Asn Asn Asp Arg Leu Glu G ly Ala Glu Ile Glu Glu
                180                 185                 190

Phe Leu Arg Arg Leu Leu Lys Arg Pro Glu L eu Glu Glu Ile Phe His
            195                 200                 205

Gln Tyr Ser Gly Glu Asp Arg Val Leu Ser A la Pro Glu Leu Leu Glu
        210                 215                 220

Phe Leu Glu Asp Gln Gly Glu Glu Gly Ala T hr Leu Ala Arg Ala Gln
225                 230                 235                 240

Gln Leu Ile Gln Thr Tyr Glu Leu Asn Glu T hr Ala Lys Gln His Glu
                245                 250                 255

Leu Met Thr Leu Asp Gly Phe Met Met Tyr L eu Leu Ser Pro Glu Gly
                260                 265                 270

Thr Ala Leu Asp Asn Thr His Thr Cys Val P he Gln Asp Met Asn Gln
            275                 280                 285

Pro Leu Ala His Tyr Phe Ile Ser Ser Ser H is Asn Thr Tyr Leu Thr
        290                 295                 300
```

-continued

```
Asp Ser Gln Ile Gly Gly Pro Ser Ser Thr Glu Ala Tyr Val Arg Ala
305                 310                 315                 320

Phe Ala Gln Gly Cys Arg Cys Val Glu Leu Asp Cys Trp Glu Gly Pro
            325                 330                 335

Gly Gly Glu Pro Val Ile Tyr His Gly His Thr Leu Thr Ser Lys Ile
            340                 345                 350

Leu Phe Arg Asp Val Ala Gln Ala Val Arg Asp His Ala Phe Thr Leu
        355                 360                 365

Ser Pro Tyr Pro Val Ile Leu Ser Leu Glu Asn His Cys Gly Leu Glu
370                 375                 380

Gln Gln Ala Ala Met Ala Arg His Leu Cys Thr Ile Leu Gly Asp Met
385                 390                 395                 400

Leu Val Thr Gln Ala Leu Asp Ser Pro Asn Pro Glu Glu Leu Pro Ser
            405                 410                 415

Pro Glu Gln Leu Lys Gly Arg Val Leu Val Lys Gly Lys Lys Leu Pro
            420                 425                 430

Ala Ala Arg Ser Glu Asp Gly Arg Ala Leu Ser Asp Arg Glu Glu Gly
            435                 440                 445

Glu Glu Asp Asp Glu Glu Glu Glu Glu Val Glu Ala Ala Ala Gln
450                 455                 460

Arg Arg Leu Ala Lys Gln Ile Ser Pro Glu Leu Ser Ala Leu Ala Val
465                 470                 475                 480

Tyr Cys His Ala Thr Arg Leu Arg Thr Leu His Pro Ala Pro Asn Ala
            485                 490                 495

Pro Gln Pro Cys Gln Val Ser Ser Leu Ser Glu Arg Lys Ala Lys Lys
            500                 505                 510

Leu Ile Arg Glu Ala Gly Asn Ser Phe Val Arg His Asn Ala Arg Gln
            515                 520                 525

Leu Thr Arg Val Tyr Pro Leu Gly Leu Arg Met Asn Ser Ala Asn Tyr
        530                 535                 540

Ser Pro Gln Glu Met Trp Asn Ser Gly Cys Gln Leu Val Ala Leu Asn
545                 550                 555                 560

Phe Gln Thr Pro Gly Tyr Glu Met Asp Leu Asn Ala Gly Arg Phe Leu
            565                 570                 575

Val Asn Gly Gln Cys Gly Tyr Val Leu Lys Pro Ala Cys Leu Arg Gln
            580                 585                 590

Pro Asp Ser Thr Phe Asp Pro Glu Tyr Pro Gly Pro Pro Arg Thr Thr
        595                 600                 605

Leu Ser Ile Gln Val Leu Thr Ala Gln Gln Leu Pro Lys Leu Asn Ala
        610                 615                 620

Glu Lys Pro His Ser Ile Val Asp Pro Leu Val Arg Ile Glu Ile His
625                 630                 635                 640

Gly Val Pro Ala Asp Cys Ala Arg Gln Glu Thr Asp Tyr Val Leu Asn
            645                 650                 655

Asn Gly Phe Asn Pro Arg Trp Gly Gln Thr Leu Gln Phe Gln Leu Arg
            660                 665                 670

Ala Pro Glu Leu Ala Leu Val Arg Phe Val Val Glu Asp Tyr Asp Ala
        675                 680                 685

Thr Ser Pro Asn Asp Phe Val Gly Gln Phe Thr Leu Pro Leu Ser Ser
        690                 695                 700

Leu Lys Gln Gly Tyr Arg His Ile His Leu Leu Ser Lys Asp Gly Ala
705                 710                 715                 720

Ser Leu Ser Pro Ala Thr Leu Phe Ile Gln Ile Arg Ile Gln Arg Ser
```

-continued

```
                725          730          735
```

<210> SEQ ID NO 3
<211> LENGTH: 13953
<212> TYPE: DNA
<213> ORGANISM: Human

<400> SEQUENCE: 3

| | | | | | |
|---|---|---|---|---|---|
| ttcccccaac | aggttcctgg | ggagctgagg | gtaaggggcc | agaagtaggg g | ccccctcca | 60 |
| ttgggagcct | gcccaagtgg | gggcccagtc | aggcgttcag | gctgcctgtg t | tgatggcct | 120 |
| gtttgcagaa | ggctctggac | agagcaggcc | ccggtgactc | accccccattt c | cggccttag | 180 |
| tcactcatct | cccccacacc | catgggcttg | gcatcagagg | gctggcctag g | taggggagg | 240 |
| cagccccagc | tgcagagcct | ggttgtcatg | gcaatgagca | gtccccccttc c | catggccaa | 300 |
| ggggtgtag | gaggatgtgc | ctaagtgtag | tggcgctgca | ggctcccctc t | gccctcacc | 360 |
| gtgtcattgc | tcaggatggg | accatttaga | ggctacctgg | acctggtggg g | ggggggggt | 420 |
| ctggtgagcc | cctcggcctg | gcacgtgccg | tgtacaccca | gctctttgtc t | ggaaagagg | 480 |
| agggttccac | tttccccttc | ctgaccaggg | ggtaccgagt | gggcattcac t | cagagggcc | 540 |
| acagtctaga | ccctgaggga | ccctctggag | ctgttagggc | cacaggctgg c | cccaagggg | 600 |
| tcatggcctc | ttaaggaggt | ggatttctcc | tcttgcccct | gagaccctga t | tttcagtca | 660 |
| tggtcaaagt | gggttttaaa | aatacagatg | cccaggcccc | atcccacacc a | gctgggtga | 720 |
| gatgccctgg | gctgtggtgt | ctgcagcctc | ccctgggtaa | ttccgatgca c | agctaaggt | 780 |
| tgagaaaccc | tgacctgcga | ggcctctgcc | ctgcgaggcc | tctgccctga a | ctctggaca | 840 |
| gatggggcag | agctggggat | agaattcact | tagtcccccc | atctgtccgt c | tacctgtct | 900 |
| gccccttcag | tcaacactag | ctggtatcct | ggctctggga | tgagcactgt g | gtgaggaga | 960 |
| taagacctca | ttccgccctc | agatttatta | agtatatag | gtgggttttg t | gttttattt | 1020 |
| taattaaagc | aaaaagtgct | gttagtggtc | agagagggag | aatgtccact t | gaggacaaa | 1080 |
| tcaaggaagg | gttcctggag | gagtgatat | ctgaactggt | ccttcaagga c | tcagatagg | 1140 |
| aggaagagaa | gggagaagga | tcctacaaaa | gggtccaaga | gagggtgaga g | gagatggtc | 1200 |
| cagagatata | gactcaattc | cttaggtcag | aatttgcaat | tgggcaagcc a | gggccttgg | 1260 |
| ggtcacaaag | ccaaacccag | tattagggc | ttgtcgaaat | aaagggagga a | gagaggccc | 1320 |
| tctgtcttac | ttcttttggc | ccacacaggg | gttattgatt | tttatttttt t | tcaatttga | 1380 |
| tttcgttgtc | aacattagaa | tatctggagg | cttcacacac | agatctatat t | cggttctct | 1440 |
| ggaaactccg | ggccctcatt | cactccgggc | tgtgccccac | ctccaaaggc c | atggactct | 1500 |
| ccgtttaccc | agttcccacc | tcctctattg | tcctctgact | caaaaatctt t | ggttgtgac | 1560 |
| tctcgttgag | gcattgtaga | gcagggtgtg | gcactgtttg | ggctgggcat c | acgtgttcc | 1620 |
| aggggccag | agccaggaga | gggccgaaac | tctccggggc | acagtgtcgg t | cacgctgta | 1680 |
| gaaacctctg | aattttggat | tttgcagcag | gtatgattgt | ggtctccatt t | tatggatgg | 1740 |
| agaacatgag | gcttagtgac | aggttagtgc | cactggggcc | atgtattaaa t | aactgggaa | 1800 |
| gtgacagtgt | tgagacttac | tcccccagact | tcggaattca | gaagcactag a | agagccgtg | 1860 |
| cagtgcaggg | ccaaaggtca | gaggcgctgg | accccgacct | ccagagccca a | gtggcttc | 1920 |
| taccagtatg | gaattctgac | aacttactta | agcttccctg | agcctcagtt t | ccttgtctg | 1980 |
| ttagtacatg | agcagggcct | gcacacagga | gatgctttta | tttatttatt t | tttagagac | 2040 |
| agagtctcac | tctgttgccc | aagctggagt | gcagtggcgc | aatcttggct c | actgcaacc | 2100 |

-continued

```
tccgcctccc ggattcaagt gattctcatg cctcagcctc ccatgcctgg a gatcagctg    2160 ggcagggctg atcctggagt ccttggcctg tgaccctgga gccagggtgg c ctctgctgt    2220 cctccttgtc tttgggaaag cagaggcaag gtgcttgggt tacagcaaga g agatctagg    2280 ttagatggtg agaccttcct gatggctacg gtttcacatc aagggaaaaa g gctgttggt    2340 ggcaaattct ggacttgaag gctggaagcc atgtggtggg gatagtggc a gaaaaggca    2400 attttttttt ttttttgtta agacgcagtc tcactctgtc gcttaggctg c agtgcagtg    2460 gcacaatctt ggctcatggc aacctcagcc tcctaagtag ctgggattac a ggcatgtgc    2520 caccacaccc agctaatttt gtattttag tagaggtggg gttgcaccat g ttggccagg    2580 ctggtctcga actcccgacc tcaagtgatc cacccacctc ggcctcccaa g tgctgagat    2640 tacaggcgtg cagccgcgcc ctgccagaaa gggaaccttt agtgaggcct g agtcccagg    2700 cattgtccga gggcagttcc acactgaggg actgcagagg ccgctgcttg g aaggaagga    2760 gggagatggg gtacgggttg gggggcgctt agggctccaa agcctaaagc c aaacccagt    2820 gcaggaggct tcttacaatc ggggaggagg ggagtcctgt gagggggagg g aagcttact    2880 gtgggatgaa ggcctgggtt tggagaggct ggaggatggg gcagcaggtc t atcgggg     2940 agggcagggg agcctctggg caggtacggc ctgacgcccc gggtcctccc g ccccgccag    3000 gcctgacgga ggacgaggac gtgcgcgcca tgctgcgggg ctcccggctc c gcaagatcc    3060 gctcgcgcac gtggcacaag gagcggctgt accggctgca ggaggacggc c tgagcgtgt    3120 ggttccagcg gcgcatcccg cgtgcgccat cgcagcacat ctgtgagagg c cggggagcg    3180 ccgggcggac agggaggtgg ggacaggccc ggtcctccgc cctgacccgg c cctcctctc    3240 agtcttcgtg cagcacatcg aggcggtccg cgagggccac cagtccgagg g cctgcggcg    3300 cttcggggt gccttcgcgc cagcgcgctg cctcaccatc gccttcaagg g ccgccgcaa    3360 gaacctggac ctggcggcgc ccacggctga ggaagcgcag cgctgggtgc g cggtctgac    3420 caagctccgc gcgcgcctgg acgccatgag ccagcgcgag cggctagacc a atatcctgc    3480 cggggctggg agggagggcc ccatccttgg agagccctaa ccttggagag c cccatcctt    3540 ggagagcccc cacgcccagg gaaggcaggg cccctgtcct gagggcgcac g gtctgggtc    3600 ggagcccttg gtcttcgaaa ctgagggtgg ggacacgcgc cctggctagg c ccaagctcc    3660 caccaggagg ggtggcgcgg cgcctccttc agggaggcct gaggccttct g agggtgaag    3720 acagggcctc ctgtctttgg taagcccag tcctgcggag gagacactgc t accgtgctc    3780 ggggagtgca caggccaagg ggaaagtaca gccctaaac tggggatccc c cagacccag    3840 gtgggggtga cttaccagcc agttacctga gggctggggg cagcctggcg t gttgctgtt    3900 atttcctgag cacccacacc tggatccact cctatctgca ccgggctgac t ccaaccagg    3960 acagcaagat gagcttcaag gagatcaaga gcctgctgag aatggtcaac g tggacatga    4020 acgacatgta cgcctacctc ctcttcaagg tgggcttccg ccctgaaccc c agccctgg    4080 ctctgccatc actctgacct ctgcctgccc ccagccatct gaatcatcag c tccctgcc    4140 ctctccatct gcagcttttt tggagcgagc agccttccc tgcacaaagg c aacatctgg    4200 ggttagttag ccttttgcct ccctgaggc cactgggcca ggaagggagt g gggagccgg    4260 ggcccagaac tttcctcatc ctcagttcct accctccaa agtgagcagc a aagctgttt    4320 tcatttccct gagtctgcaa ggcacctttt gcacgtgggg gcacaggcag g agccagcct    4380 acaggtgtgc atgtgcacgg atacacgtgt gcacccttct ccacgcagac c ctccactgt    4440
```

```
ggcacgtgtt ggcacctcat gcatgggagc acagggcac acaggagtgg g ctctgcagc   4500
tatggcccag ctggagccca tggcagacct ctgtgtgcat gtggatggtg g gacccacct   4560
gtgaccccga agacaggag agcccatggc agctggaccc ctgggccaca g cttcacagg   4620
gatgctccat gaattctcat tgacttgttc aatgacgctg ggtgtgaata t gtgcatgtc   4680
aggatagtaa cgtgtccacc tagggggagtg tgagggccca agggccctgt c ttggcccag   4740
ggtcaccatt tttccttcca catcttgatt cctggggtag gtcatggtgc a gaggggcag   4800
gcactgaacc agagagacct tttaagtcca gccctgccgg ccaggctcag t ggctcaccc   4860
ctgtcatccc agcactttga gaggcctagg cgggaggatt gcttgaagcc a ggagtttga   4920
gatcagcttg gcaacacag caagaccca tctctacaaa aaatacaaaa a ttagccagg   4980
tgcagtggtg cacaccagtg gtcccagctg tccagctatt tggaaggctg a ggtgggagg   5040
atcacttgag atcacgcgtt ggaagctgca gtgagctatg atcatgccac t gcgctccag   5100
cctgggtaac agagcaagac caaacaaaca aacaaaccta aaaaacaaac c aaaaagtcc   5160
tgccctgtaa tttaccagct gtgtgagcta gagtcacaag tcttactctg t ttttccacc   5220
tgtgaaatgg ggaccattgc cttctcagat gtggtagatg acagatgggt c aaagggcc   5280
aggtttcctg gagtgtctgc ctcctctgag cttctcctgc tgctccccag g agtgtgacc   5340
actccaacaa cgaccgtcta gaggggctg agatcgagga gttcctgcgg c ggctgctga   5400
agcggccgga gctggaggag atcttccatc agtactcggg cgaggaccgc g tgctgagtg   5460
cccctgagct gctggagttc ctggaggacc agggcgagga gggcgccaca c tggcccgcg   5520
cccagcagct cattcagacc tatgagctca cgagacagg tggggggggt g gcacggcca   5580
ggtcgtggca cctgaaaggg ctgtgttccc agctaagcgg gttctgctgc g ggctggcgc   5640
gggcatcatc tcgggcaggt tacctcacct cctccagact cagcttccac a tgtgtaaaa   5700
tggcacaaca gtttgtcttc ctcccagggt ctggtcgaag gttaagtggc a tgacttacg   5760
tggagtctag tcagtagatt gtctagtcat tattcctaag ctgagtgggc c ttggggca   5820
ttggaagctg gacatggggg atccctatgt ggcctgatgc cctctcctgc c accctgca   5880
gccaagcagc atgagctgat gacactggat ggcttcatga tgtacctgtt g tcgccggag   5940
ggggctgcct tggacaacac ccacgcgtgt gtgttccagg acatgaacca g ccccttgcc   6000
cactacttca tctcttcctc ccacaacacc tatctgactg actcccagat c gggggcccc   6060
agcagcaccg aggcctatgt taggtactgt agcaggggt gaatgtttcc g ggagcccca   6120
cctggggaga gacatgggct ggcttcctgg ggccttcctg gcccagcctg c ctgctgccc   6180
tgctctgtgg cactctggca acaccttgcc cgtccaccca tctgtccaca c acagggcct   6240
ttgcccaggg atgccgctgc gtggagctgg actgctggga ggggccagga g gggagcccg   6300
tcatctatca tggccatacc ctcacctcca agattctctt ccgggacgtg g tccaagccg   6360
tgcgcgacca tgccttcacg gtgagcccct gggatgccca gccccagccc c acagccttc   6420
ccaatgacct ccgtccgcac tcacatgcca gctgccctcc gtccttccag a ggaaaccct   6480
tgcccagaga atcattcatt caccaagtgc tgctgggata agtggccaat g gggtggcat   6540
aaagctgaat gagatgccac cctcatattt gggaaatatg ttccctctct c atatttggg   6600
aaatgtccta aaaatcacag agtttccaga agaaaacctt tggggagggg a aggacattt   6660
taatcatgac ttccaaagaa taaataagct gtaagagaag ctcaccagtg g catctgcat   6720
aaacactgca actttggtca cagtgtgcaa atcttcccat cagcaaatga t gggaggaga   6780
gttttcacat cactgacata gtcaatgtca ttcacatgta aaaagcattt a tgggaccag   6840
```

```
gtgcggtggc tcacacccgt attcccagca ctctgggagg ctgacgcgag g atcacttga   6900 ggccaggaat tccagaccag cctgagcaaa tagctacatc ctgtctcaac a aaaataaaa   6960 attagctgag tgtgggggca tgtgcctgta ggctgagtta ctcaggaggc t gaggtgggg   7020 ggatcacttg agcccaggac tggagaacac agggagactg actgtgccac t gcacttcag   7080 cctgggtgat ggagagagac caaagcatag acaacaacaa caaaaaatcg g ccaggcgtg   7140 gtggctctca cctgtaatcc cagcactttg ggaggctgag gtgggcagat c acctgaggt   7200 caggagtttg agaccagcct ggccaacatg gtgaaacctc atctctatta a aaatacaaa   7260 aattagccgg gtgtggtggc gggcgcctgt aatcccagct acttaggagg c tgaggcagg   7320 gagaatcgct tgaacccggg agatggaatt gtagtgagct gagattgcac c actatactc   7380 cagcatgggc gacagagcaa cactccatct caaagaaaaa aaaataatt c ctgcagccg   7440 ccctcagcct cctggacagt ctgctgcttc cctgggttct ccagagccct g cctttgcct   7500 gcctgtcctg aagggtctgg gagccagatg ttgggagata ctggcagagg g aggggagtg   7560 gctctgagct gctgcccttc cccccacagc tgtccccttta ccctgtcatc c tatccctgg   7620 agaaccactg cgggctggag cagcaggctg ccatggcccg ccacctctgc a ccatcctgg   7680 gggacatgct ggtgacacag gcgctggact ccccaaatcc cgaggagctg c catccccag   7740 aggtgacgcc ccccagcccc tagtctgggt ggagggaggt ctggtgggag t ccgcctccc   7800 cgcactgctc gtgccacctc tgtggctcag gaccoctcac ctcttgctgc c ttaacttttt   7860 ctctgttcct ctgttcatct gaggtctgcc atcccctggt cttgtccttc t gctgccctc   7920 tggctctcca ttcttgacta daccccccca cacacacacc ctcttctgta a cctggcttt   7980 gccctgctgg ccctgtgtcc ctgcccgtag agtcctgcag gctctgccat t cccacctgc   8040 aaggcccegc ttgacactt ctccacctgg aagtcccttc tcggccatcc a cacttgcca   8100 agcgtcacct gcttagaatt cagctcaact tcagccgcct cttcctgtgg c cttatccac   8160 ttccccaact ctcgggcctg aggcggcctc ctgctctccc ccagacacca g agcgcgtcc   8220 tcggctctct ccagacattt atcctgtcgg gctccttgag aaaactctcc t cctacttcc   8280 aatccccaac atgcaggcag ggttgactca ccctcgtgtg tgtgtgagat g tgattttttg   8340 ttattactgt gaaaatcaca cccgtatggt aaaagaaaac tgagctgtac t aagggacgc   8400 gatgagcagt gctcccctcc ctccactgac ctgtcctctt tcacaagaag t aaccatctc   8460 taactttctt gcatgtcctt caagaatttc cccacacaca ttacctgtgt a catatgtgt   8520 actgtcttct ctttttaaatg gtaccaaaaa aggacatgtg attccaggtt g tagcctcac   8580 ttcttccacg taagatcttc ttttgaagagg gtccctttcc tttcagtcct g agctgtcgc   8640 gtgcattgta gtggctgctg tgtatattct gatgttgagg gaccttatta a gcatccctt   8700 cctgatggcc tccgggccca ttctccactc ttttcctatta gaaacatcgc t catctctgt   8760 gtctcctttc ctgcctccca cccctagcca gcccctcaca aggcggtggt t gaataactg   8820 actgactggc tgccacaggg gcgagaaggc ctaacccttc atcctccacg t ggcccccca   8880 cagcagctga agggccgggt cctggtgaag ggaaagaagc tgcccgctgc t cggagcgag   8940 gatgccgggc tctgtcgga tcgggaggag gaggaggagg atgacgagga g gaagaagag   9000 gaggtggagg ctgcagcgca gaggcggctg gtgagagctg ggatgggtgg g gtggggaag   9060 gggggggaagg tgggaggacg gatgtgggaa gcggggccca gctgaaccccc g ctgagcctg   9120 gtctcctagg ccaagcagat ctccccggag ctgtcggccc tggctgtgta c tgccacgcc   9180
```

-continued

```
acccgcctgc ggaccctgca ccctgccccc aacgccccac aaccctgcca g gtcagctcc    9240 ctcagcgagc gcaaagccaa gaaactcatt cgggaggcag gtaggagctg g ggcactggg    9300 tgtctggggg cgagagggtg agagacctcc tgaagggagt ctggaaagga g ttgaggggg    9360 ctttggggga cagtaaagag gtcaagagga ccccaaagag gggctgggct g agggaatga    9420 gggccccgca catgccaggg tggatggagg ggagtggcac gctgagggcg g cctgctgtc    9480 tgccttcaga gccctgtggt ggggccggcc atagagggtg atgggtcagg c tgggctggg    9540 ggctggggga gcccagcagc tgctgcaaca ctggggagga attcctgggg c aggtgatgc    9600 tgagaggaca catcacctgg aggactagga agcagccagg tgaagagggg a gagcgcttt    9660 ccagacagga ggaacaggtt gttgaaggcc tggggccttg gcctggagaa g aattccagg    9720 aaccacagtg gagctggagg gccgtgggca ttcagtgtac ttggttggaa c tttgtcagg    9780 agctgggaat tggggctggg ggatgcaggg ccaggctgtg tggctggagg g ggtccctgc    9840 agcctcctca gtgagctccc ctctcactct aggtcagaag agagtgagga g cgggggcag    9900 ggtgacctgg ggacgggctt gggctctgtt ccctggaggt tacaggccgg g gctttgggt    9960 gagggacccc cggagtctgt cacggtctca ccccaactct gccccaggga a cagctttgt   10020 caggcacaat gcccgccagc tgacccgcgt gtacccgctg gggctgcgga t gaactcagc   10080 caactacagt ccccaggaga tgtggaactc gggctgtcag ctgggtaagt g ggggccaca   10140 ggaatgagag caggcggggt gccacagtgt gggggaggcc tcagcagtga g gggcccaca   10200 cagccttcca gacggtggaa acacgcattt tgttgattat ttttaaagtt g ccagcaatg   10260 taggtgggaa aatcaaatca ggctcgtttg ttcttgacag tgtacaggtc t cgcattttt   10320 atcatggtag aaattaaaat ctccactccc atgtcccccg gacacacaca a ccccccacac   10380 acctggcagt cccactaagt caacactgac aagggtgggc tctgggggac g ctgagcccc   10440 accaaaggag ggctgtatcg tctccttggg gtaaggatgg aaaccccagg c ttcctcaga   10500 cccctggctc tgacccaagc ctggccctga gggtggggc ttttttagta c ctcccaccc   10560 cagtcttgag ggatcccagg gcagaagtac aggtgacagt ggggggctggg t ccatgaccc   10620 cctcccctaa agtcatggtg ggagcagagc agcactaagc agacagtggg a cccaggcc   10680 ctttgtagag aggaatgcag tccctgaaa ctgagtagtg agaacagggc c gctaagagc   10740 ccctgctctg accctgctgt gtccacagtg gccttgaact tccagacgcc a ggctacgag   10800 atggacctca atgccgggcg cttcctagtc aatgggcagt gtggctacgt c ctaaaacct   10860 gcctgcctgc ggcaacctga ctcgaccttt gaccccgagt acccaggacc t cccagaacc   10920 actctcagca tccaggtcag caggctgaac cgggccccag tgtggggtca g actggttct   10980 agaaaggctc tttgtgaggt ggaggaaggc aagggaggct ggggacattt g gaagtgagg   11040 gtggtgtgag cttgaggccc atgagggat ggccaaggtg ggcgtgggcc c cagccactc   11100 cctccctcac ccacaggtgc tgactgcaca gcagctgccc aagctgaatg c cgagaagcc   11160 acactccatt gtggaccccc tggtgcgcat tgagatccat ggggtgcccg c agactgtgc   11220 ccggcaggag actgactacg tgctcaacaa tggtgggcag ccactggcgg a agtggggtt   11280 gggggagact gcagagagcg aagggtggtg caggtgggt cctggggccc c tgggctctg   11340 actgccatcc ctgtgcccta ggcttcaacc cccgctgggg gcagaccctg c agttccagc   11400 tgcgggctcc ggagctggca ctggtccggt ttgtggtgga agattatgac g ccacctccc   11460 ccaatgactt tgtgggccag tttacactgc ctcttagcag cctaaagcaa g gttggtgga   11520 ggctggtggg gatggagagg gatgtgggtc caggtcctgc agaccctgtt c acctttgtg   11580
```

```
cctcgaattt cctgccctga agcaggcccg ggctgggcca gacccccagg g tgcacagag  11640 gacctgaggc ctggctgtcc tccctacagg gtaccgccac atacacctgc t ttccaagga  11700 cggggcctca ctgtcaccag ccacgctctt catccaaatc cgcatccagc g ctcctgagg  11760 gcccacctca ctcgccttgg ggttctgcga gtgccagtcc acatcccctg c agagccctc  11820 tcctcctctg gagtcaggtg gtgggagtac cagccccccca gcccacccac t tggcccact  11880 cagcccattc accaggcgct ggtctcacct gggtgctgag ggctgcctgg g cccctcctg  11940 aagaacagaa aggtgttcat gtgacttcag tgagctccaa ccctggggcc t gagatggc   12000 cccagctcct cttgtcctca gcccacccct cattgtgact tatgaggagc a agcctgttg  12060 ctgccaggag acttggggag caggacactt gtgggccctc agttccctc t gtcctcccg    12120 tgggccatcc cagcctcctt cccccagagg agcgcagtca ctccacttgg c cccgaccc    12180 gagcttagcc cctaagccct cctttacccc aggccttcct ggactcctcc c tccagctcc  12240 ggaacctgag ctcccctcc cttctcaaag caagaaggga gcgctgaggc a tgaagccct   12300 ggggaaactg gcagtaggtt ttggttttta ttttttgaga cagggtctcg c tccgtcgcc  12360 caggctggag tgcaatgttg caatcatggc tcactgcagc tttgaactcc c aggctcaag  12420 cgatcctccc atctcagcct cctgagtagc tgggactaca ggcacaggcc a ccaaacctg  12480 gctaatgttt aaattttatg tagagatggc gggggggcg gggtctccc t atgttgccc    12540 aggctggtct cgagctcctg acctcaagtg atcctcctgc cccagcattc c aaagtgctg  12600 ggattacagg tgtgagccac tgcctggcct ggccgtaggt ttgtaactgt t tcatagaag  12660 agccctggag aagacagtag aatgagccta tctagtttaa aaaataaaga a gcacgttga  12720 tttcaccacc gccactccct gagcacctct atgctgccac cccacaggc c catgaggag    12780 ggacagggct ggatgagttt cttgggcctc tcccctcaac agggcatgga c ttggctaag  12840 acagccaggg ggtggcagca ggagatgcca cagctctaaa tagcccgatc c ctgctcctg  12900 gcttaaagct gctgcgagta tcacaagact gtctgaggat gccaattcag c aggtcagcg  12960 cctccccaca acacacacac acacacacac acacacacac tcacacatac a cagagggc   13020 cttgaatgag gaggagacag gagtctgagg gaccctcaga ctgccactct c caggcttgg  13080 ctgggctcaa ggccctgtc tgctcagtag ggcaaatccc aaggacacgg g cttcccttc    13140 ctccagccag ccagccttt acacaaaggc tggaaacgct gcttgggccg c ctctataga   13200 aatgccagga gagcgcactg gacactaggc gacagaatct ggagaaaatc c tgcacccgc  13260 ccctgccagc agggtgaaat gtggaggcct ggtgtttag gttctgccag c caacagtgc   13320 cggcactgga caagggcaga acttgacatt agtccccaga gggtggcctg g aactgggct  13380 gggataggcc ttgaactggc cccaagcccc acagaaacca aaacacaggg c tggggcaga  13440 ctccaccttc tagcaactcc aagaactaat gcagaaagtg gcagtgtccc c cgctccttc  13500 atgctgggag tggcgtttgg ctctggttaa tttgtgtgtc tgaaagagga t aatcagaat  13560 caaaagggca cagaaggaat gggccgagcc aggcgggccg ggcaggcag c ccgggcatc    13620 tggccctcag ggctgtcaga gggtcaggct gccaaactgc agcctcagga t gggaggcac  13680 agtgaggcta agtccagttt tagcaaatga agagccatta gcattcccca g cccctgcag  13740 agccaggtct ggccagggc tggctggggg gtctgggtca ggtgagcacc a gacccaggg   13800 ctgagtgccc atcctgcttg gcttctctgg tttcgtatct ggtaccaaga g gaaggggtg  13860 aaggctagga tgagggccca atactgagaa ggctgccttg aaagggcaag a gtctttttt  13920
```
tttttttctt ttgagacaaa gtcttgctcg tcc       13953

<210> SEQ ID NO 4
<211> LENGTH: 744
<212> TYPE: PRT
<213> ORGANISM: Cricetulus griseus

<400> SEQUENCE: 4

Gly Leu Gln Asp Asp Gln Asp Leu Gln Ala Leu Leu Lys Gly Ser Gln
 1               5                  10                  15

Leu Leu Lys Val Lys Ser Ser Trp Arg Arg Glu Arg Phe Tyr Lys
            20                  25                  30

Leu Gln Glu Asp Cys Lys Thr Ile Trp Gln Glu Ser Arg Lys Val Met
        35                  40                  45

Arg Ser Pro Glu Ser Gln Leu Phe Ser Ile Glu Asp Ile Gln Glu Val
    50                  55                  60

Arg Met Gly His Arg Thr Glu Gly Leu Lys Phe Ala Arg Asp Ile
65                  70                  75                  80

Pro Glu Asp Arg Cys Phe Ser Ile Val Phe Lys Asp Gln Arg Asn Thr
                85                  90                  95

Leu Asp Leu Ile Ala Pro Ser Ser Ala Asp Ala Gln His Trp Val Gln
            100                 105                 110

Gly Leu Arg Lys Ile Ile His His Ser Gly Ser Met Asp Gln Arg Gln
        115                 120                 125

Lys Leu Gln His Trp Ile His Ser Cys Leu Arg Lys Ala Asp Lys Asn
    130                 135                 140

Lys Asp Asn Lys Met Asn Phe Lys Glu Leu Lys Asp Phe Leu Lys Glu
145                 150                 155                 160

Leu Asn Ile Gln Val Asp Asp Ser Tyr Ala Arg Lys Ile Phe Arg Glu
                165                 170                 175

Cys Asp His Ser Gln Thr Asp Ser Leu Glu Asp Glu Glu Ile Glu Thr
            180                 185                 190

Phe Tyr Lys Met Leu Thr Gln Arg Ala Glu Ile Asp Arg Val Phe Ala
        195                 200                 205

Glu Ala Ala Gly Ser Ala Glu Thr Leu Ser Val Glu Lys Leu Val Thr
    210                 215                 220

Phe Leu Gln His Gln Gln Arg Glu Glu Ala Ala Gly Pro Ala Leu Ala
225                 230                 235                 240

Leu Ser Leu Ile Glu Arg Tyr Glu Pro Ser Glu Thr Ala Lys Ala Gln
                245                 250                 255

Arg Gln Met Thr Lys Asp Gly Phe Leu Met Tyr Leu Leu Ser Ala Asp
            260                 265                 270

Gly Ser Ala Phe Ser Leu Ala His Arg Arg Val Tyr Gln Asp Met Asp
        275                 280                 285

Gln Pro Leu Ser His Tyr Leu Val Ser Ser Ser His Asn Thr Tyr Leu
    290                 295                 300

Leu Glu Asp Gln Leu Thr Gly Pro Ser Ser Thr Glu Ala Tyr Ile Arg
305                 310                 315                 320

Ala Leu Cys Lys Gly Cys Arg Cys Leu Glu Leu Asp Cys Trp Asp Gly
                325                 330                 335

Pro Asn Gln Glu Pro Ile Ile Tyr His Gly Tyr Thr Phe Thr Ser Lys
            340                 345                 350

Ile Leu Phe Tyr Asp Val Leu Arg Ala Ile Arg Asp Tyr Ala Phe Lys
        355                 360                 365

-continued

```
Ala Ser Pro Tyr Pro Val Ile Leu Ser Leu Glu Asn His Cys Ser Leu
        370                 375                 380
Glu Gln Gln Gln Val Met Ala Arg His Leu Lys Ala Ile Leu Gly Pro
385                 390                 395                 400
Met Leu Leu Asp Gln Pro Leu Asp Gly Val Thr Met Ser Leu Pro Ser
                405                 410                 415
Pro Glu Gln Leu Lys Gly Lys Ile Leu Leu Lys Gly Lys Lys Phe Gly
            420                 425                 430
Gly Leu Leu Pro Ala Gly Gly Glu Asn Gly Pro Glu Thr Thr Asp Val
            435                 440                 445
Ser Asp Glu Asp Glu Ala Ala Glu Met Glu Asp Glu Ala Val Arg Ser
        450                 455                 460
Gln Val Gln Gln Lys Ser Lys Glu Asp Lys Leu Asn Val Ala Pro Glu
465                 470                 475                 480
Leu Ser Asp Met Val Ile Tyr Cys Lys Ser Val His Phe Gly Gly Phe
                485                 490                 495
Ser Asn Pro Ser Thr Ser Gly Gln Ala Phe Tyr Glu Met Ala Ser Phe
            500                 505                 510
Ser Glu Asn Arg Ala Leu Arg Leu Leu Gln Glu Ser Gly Asn Asn Phe
        515                 520                 525
Val Arg His Asn Val Ser His Leu Ser Arg Ile Tyr Pro Ala Gly Arg
        530                 535                 540
Arg Thr Asp Ser Ser Asn Tyr Ser Pro Val Glu Met Trp Asn Gly Gly
545                 550                 555                 560
Cys Gln Ile Val Ala Leu Asn Phe Gln Thr Pro Gly Pro Glu Met Asp
                565                 570                 575
Val Tyr Leu Gly Arg Phe Gln Asp Asn Gly Ala Cys Gly Tyr Val Leu
            580                 585                 590
Lys Pro Ala Phe Leu Arg Asp Pro Asp Thr Ala Phe Asn Pro Arg Ala
            595                 600                 605
Leu Thr Gln Gly Pro Trp Trp Ala Gln Lys Arg Leu Arg Val Arg Val
        610                 615                 620
Ile Ser Gly Gln Gln Leu Pro Lys Val Asn Lys Ser Lys Asn Ser Ile
625                 630                 635                 640
Val Asp Pro Lys Val Ile Val Glu Val His Gly Val Gly Asp Val
                645                 650                 655
Ala Ser Arg Gln Thr Ala Val Ile Thr Asn Asn Gly Phe Asn Pro Trp
            660                 665                 670
Trp Asp Thr Glu Phe Glu Phe Glu Val Ala Val Pro Asp Leu Ala Leu
            675                 680                 685
Val Arg Phe Val Val Glu Asp Tyr Asp Ala Ser Ser Lys Asn Asp Phe
        690                 695                 700
Ile Gly Gln Ser Thr Ile Pro Trp Asn Ser Leu Lys Gln Gly Tyr Arg
705                 710                 715                 720
His Val His Leu Leu Ser Lys Asn Gly Asp Gln His Pro Ser Ala Thr
                725                 730                 735
Leu Phe Val Lys Ile Ser Leu Gln
            740

<210> SEQ ID NO 5
<211> LENGTH: 744
<212> TYPE: PRT
<213> ORGANISM: Mus musculus

<400> SEQUENCE: 5
```

```
Gly Leu Gln Asp Asp Pro Asp Leu Gln Ala Leu Leu Lys Gly Ser Gln
 1               5                  10                  15

Leu Leu Lys Val Lys Ser Ser Trp Arg Arg Glu Arg Phe Tyr Lys
            20                  25                  30

Leu Gln Glu Asp Cys Lys Thr Ile Trp Gln Glu Ser Arg Lys Val Met
             35                  40                  45

Arg Ser Pro Glu Ser Gln Leu Phe Ser Ile Glu Asp Ile Gln Glu Val
             50                  55                  60

Arg Met Gly His Arg Thr Glu Gly Leu Glu Lys Phe Ala Arg Asp Ile
 65                  70                  75                  80

Pro Glu Asp Arg Cys Phe Ser Ile Val Phe Lys Asp Gln Arg Asn Thr
                 85                  90                  95

Leu Asp Leu Ile Ala Pro Ser Pro Ala Asp Val Gln His Trp Val Gln
                100                 105                 110

Gly Leu Arg Lys Ile Ile Asp Arg Ser Gly Ser Met Asp Gln Arg Gln
                115                 120                 125

Lys Leu Gln His Trp Ile His Ser Cys Leu Arg Lys Ala Asp Lys Asn
130                 135                 140

Lys Asp Asn Lys Met Asn Phe Lys Glu Val Lys Asp Phe Leu Lys Glu
145                 150                 155                 160

Leu Asn Val Gln Val Asp Asp Ser Tyr Ala Arg Lys Ile Phe Arg Glu
                165                 170                 175

Cys Asp His Ser Gln Thr Asp Ser Leu Glu Asp Glu Glu Ile Glu Thr
                180                 185                 190

Phe Tyr Arg Met Leu Thr Gln Arg Ala Glu Ile Asp Arg Ala Phe Ala
                195                 200                 205

Glu Ala Ala Gly Ser Ala Glu Thr Leu Ser Val Glu Lys Leu Val Thr
210                 215                 220

Phe Leu Gln His Gln Gln Arg Glu Glu Glu Ala Gly Pro Ala Leu Ala
225                 230                 235                 240

Leu Ser Leu Ile Glu Arg Tyr Glu Pro Ser Glu Thr Ala Lys Ala Gln
                245                 250                 255

Arg Gln Met Thr Lys Asp Gly Phe Leu Met Tyr Leu Leu Ser Ala Asp
                260                 265                 270

Gly Asn Ala Phe Ser Leu Ala His Arg Arg Val Tyr Gln Asp Met Asn
275                 280                 285

Gln Pro Leu Ser His Tyr Leu Val Ser Ser Ser His Asn Thr Tyr Leu
                290                 295                 300

Leu Glu Asp Gln Leu Thr Gly Pro Ser Ser Thr Glu Ala Tyr Ile Arg
305                 310                 315                 320

Ala Leu Cys Lys Gly Cys Arg Cys Leu Glu Leu Asp Cys Trp Asp Gly
                325                 330                 335

Pro Asn Gln Glu Pro Ile Ile Tyr His Gly Tyr Thr Phe Thr Ser Lys
                340                 345                 350

Ile Leu Phe Cys Asp Val Leu Arg Ala Ile Arg Asp Tyr Ala Phe Lys
                355                 360                 365

Ala Ser Pro Tyr Pro Val Ile Leu Ser Leu Glu Asn His Cys Ser Leu
370                 375                 380

Glu Gln Gln Arg Val Met Ala His His Leu Arg Ala Ile Leu Gly Pro
385                 390                 395                 400

Met Leu Leu Asp Gln Pro Leu Asp Gly Val Thr Thr Ser Leu Pro Ser
                405                 410                 415
```

```
Pro Glu Gln Leu Lys Glu Lys Ile Leu Leu Lys Gly Lys Lys Leu Gly
            420                 425                 430

Gly Leu Leu Pro Ala Gly Gly Glu Asn Gly Pro Glu Ala Thr Asp Val
                435                 440                 445

Ser Asp Glu Asp Glu Ala Ala Glu Met Glu Asp Glu Ala Val Arg Ser
    450                 455                 460

Gln Val Gln His Lys Pro Lys Glu Asp Lys Leu Lys Leu Val Pro Glu
465                 470                 475                 480

Leu Ser Asp Met Val Ile Tyr Cys Lys Ser Val His Phe Gly Gly Phe
                485                 490                 495

Ser Ser Pro Ser Thr Ser Gly Gln Ala Phe Tyr Glu Met Ala Ser Phe
                500                 505                 510

Ser Glu Ser Arg Ala Leu Arg Leu Leu Gln Glu Ser Gly Asn Ser Phe
                515                 520                 525

Val Arg His Asn Val Gly His Leu Ser Arg Ile Tyr Pro Ala Gly Trp
                530                 535                 540

Arg Thr Asp Ser Ser Asn Tyr Ser Pro Val Glu Met Trp Asn Gly Gly
545                 550                 555                 560

Cys Gln Ile Val Ala Leu Asn Phe Gln Thr Pro Gly Pro Glu Met Asp
                565                 570                 575

Val Tyr Leu Gly Cys Phe Gln Asp Asn Gly Gly Cys Gly Tyr Val Leu
                580                 585                 590

Lys Pro Ala Phe Leu Arg Asp Pro Asp Thr Thr Phe Asn Ser Arg Ala
                595                 600                 605

Leu Thr Gln Gly Pro Trp Trp Ala Pro Lys Leu Arg Val Trp Ile
    610                 615                 620

Ile Ser Gly Gln Gln Leu Pro Lys Val Asn Lys Asn Lys Asn Ser Ile
625                 630                 635                 640

Val Asp Pro Lys Val Ile Val Glu Ile His Gly Val Gly Gln Asp Val
                645                 650                 655

Ala Ser Arg Gln Thr Ala Val Ile Thr Asn Asn Gly Phe Asn Pro Arg
                660                 665                 670

Trp Asp Thr Glu Phe Glu Phe Val Val Ala Val Pro Asp Leu Ala Leu
    675                 680                 685

Val Arg Phe Met Val Glu Asp Tyr Asp Ser Ser Ser Lys Asn Asp Phe
    690                 695                 700

Ile Gly Gln Ser Thr Ile Pro Trp Asn Ser Leu Lys Gln Gly Tyr Arg
705                 710                 715                 720

His Val His Leu Leu Ser Lys Asn Gly Asp Leu His Pro Ser Ala Thr
                725                 730                 735

Leu Phe Val Lys Ile Ser Ile Gln
                740
```

ISOLATED HUMAN PHOSPHOLIPASE PROTEINS, NUCLEIC ACID MOLECULES ENCODING HUMAN PHOSPHOLIPASE PROTEINS, AND USES THEREOF

RELATED APPLICATIONS

The present application claims priority to PROVISIONAL APPLICATION U.S. Ser. No. 60/232,632, Filed Sep. 14, 2000.

FIELD OF THE INVENTION

The present invention is in the field of phospholipase proteins that are related to the phospholipase C subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Phospholipases

There are three major families of known human phospholipase enzymes: Phospholipase A2, Phospholipase C, and Phospholipase D.

Enzymes in the Phospholipase A2 family ("PlA2") hydrolyze the sn-2 fatty acid acyl ester bond of phosphoglycerides, releasing free fatty acids and lysophospholipids. The PlA2s constitute a diverse family of enzymes with respect to sequence, function, localization and divalent cation requirements. They play an important role in a variety of cellular processes, including the digestion and metabolism of phospholipids as well as the production of precursors for inflammatory reactions. The PlA2s have been classified into at least 5 groups (although different classification schemes exist and up to 10 groups have been identified by some authorities) based on their size, structure and need for divalent cations. Groups I, II and III all contain secreted forms of PlA, which are extracellular enzymes that have a low molecular mass and require calcium ions for catalysis. Groups IV and V contain cytosolic forms of PlA2s that have a high molecular mass and do not necessarily require calcium ions.

Amongst the best characterized of the PlA2 phospholipases are digestive enzymes secreted as zymogens by the pancreas. These enzymes, which are involved in the hydrolysis of dietary phospholipids, have strong homology to the venom phospholipases of snakes. Other PlA2s play important roles in the control of signaling cascades such as the cytosolic PlA2, Group IVA enzyme ("PLA2G4A") which catalyzes the release of arachidonic acid from membrane phospholipids. Arachidonic acid serves as a precursor for a wide spectrum of biological effectors, collectively known as eicosanoids (and including the prostaglandin group of molecules) that are involved in hemodynamic regulation, inflammatory responses and other cellular processes.

Another biologically active phospholipid, platelet-activating factor ("PAF") is hydrolyzed to metabolically-inactive degradation products by the group VII PlA2 known as PAF acetylhydrolase. Deficiency of PAF acetylhydrolase has been reported in patients with systemic lupus erythematosis and increased levels of PAF have been reported in children with acute asthmatic attacks. Elevated levels of the group II PlA2 known as PLA2G2A have been reported in plasma and synovial fluid in patients with inflammatory arthritis. Studies of a mouse colon cancer model showed that alleles of the murine ortholog of this gene were able to modify the number of tumors that developed in animals with multiple intestinal neoplasia (a mouse model of the human disorder known as familial adenomtous polyposis). Subsequent studies in humans showed mutations in PLA2G2A were associated with the risk of developing colorectal cancer. PLA2G2A is presumed to act through altering cellular microenvironments within the intestinal crypts of the colonic mucosa, although the precise mechanism by which this effect is exerted is not clear.

Enzymes in the Phospholipase C ("PLC") family catalyze the hydrolysis of the plasma membrane phospholipids, phosphatidyl inositol phosphate ("PIP") or phosphatidylinositol 4,5-biphosphate ("PIP2"), generating as products the second messengers, 1,4,5-inositol triphosphate ("IP3") and 1,2-diacylglycerol ("DAG"). Molecules belonging to the PLC gene family are divided into subfamilies, PLC-beta, PLC-gamma and PLC-delta. PLC-delta is distinguished from PLC-gamma by lack of the SH2 and SH3 domains that are essential for activation of PLC-gamma by tyrosine protein kinases. PLC-delta is distinguished from PLC-beta by lack of the C-terminal region of PLC-beta that is responsible for binding and activation of G proteins. Various PLC enzymes play important roles in signal transduction cascades throughout the body. Activating signals include hormones, growth factors and neurotransmitters. One of the functions of IP2 is to modulate intracellular calcium levels while DAG is involved in the activation of certain protein kinases and can promote membrane fusion in processes involving vesicular trafficking.

The novel human protein provided by the present invention is related to the phospholipase C family, and shows a particularly high degree of similarity to enzymes of the phospholipase C-delta subclass. PLC-delta proteins may be associated with abnormal calcium homeostasis and increased intracellular calcium ion concentrations, conditions commonly associated with hypertension (Yagisawa et al, *J Hypertens* 1991 Nov;9(11):997–1004). Furthermore, the gene encoding PLC-deltal is located just distal to a region of chromosome 3 that is deleted in a lung cancer cell line (Ishikawa et al., *Cytogenet Cell Genet* 1997;78(1):58–60), suggesting an involvement in cancers such as lung cancer. Additionally, a mutation in the pleckstrin homology domain of PLC-deltal has been found in a patient with early-onset sporadic Alzheimer's diseases (Shimohama et al., *Biochem. Biophys. Res. Commun.* 245:722–728, 1998), and mutations in the pleckstrin homology domain are known to occur in Bruton agammaglobulinemia (Shimohama et al., *Biochem. Biophys. Res. Commun.* 245:722–728, 1998). For a further review of PLC proteins, particularly proteins of the PLC-delta subclass, see: Leonis et al., *Biochem Biophys Res Commun* 1996 Jul 16;224(2):382–90; Cheng et al., *J Biol Chem* 1995 Mar 10;270(10):5495–505; Suh et al., Cell 1988 Jul 15;54(2):161–9; Milting et al., J Muscle Res Cell Motil 1996 Feb;17(1):79–84; and Lyu et al., *Mammalian Genome* 7:501–504, 1996.

Enzymes in the Phospholipase D ("PLD") family catalyze the hydrolysis of phosphatidylcholine ("PC") and other phospholipids to produce phosphatidic acid. A range of agonists acting through G protein-coupled receptors and receptor tyrosine kinases stimulate this hydrolysis. Phosphatidic acid appears to be important as a second messenger capable of activating a diverse range of signaling pathways. PC-specific PLD activity has been implicated in numerous cellular pathways, including signal transduction, membrane trafficking, the regulation of mitosis, regulated secretion, cytoskeletal reorganization, transcriptional regulation and cell-cycle control. Many proteins are attached to the plasma membrane via a glysylphosphatidylinositol ("GPI") anchor. Phosphatidylinositol-glycan ("PIG")-specific PLDs selectively hydrolyze the inositol phosphate linkage, allowing release of the protein.

Phospholipase proteins, particularly members of the phospholipase C subfamily, are a major target for drug action and development. Accordingly, it is valuable to the field of pharmaceutical development to identify and characterize previously unknown members of this subfamily of phospholipase proteins. The present invention advances the state of the art by providing previously unidentified human phospholipase proteins that have homology to members of the phospholipase C subfamily.

SUMMARY OF THE INVENTION

The present invention is based in part on the identification of amino acid sequences of human phospholipase peptides and proteins that are related to the phospholipase C subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phospholipase activity in cells and tissues that express the phospholipase. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain.

DESCRIPTION OF THE FIGURE SHEETS

FIG. 1 provides the nucleotide sequence of a cDNA molecule that encodes the phospholipase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain.

FIG. 2 provides the predicted amino acid sequence of the phospholipase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phospholipase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 16 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phospholipase protein or part of a phospholipase protein and are related to the phospholipase C subfamily. Utilizing these sequences, additional genomic sequences were assembled and transcript and/or cDNA sequences were isolated and characterized. Based on this analysis, the present invention provides amino acid sequences of human phospholipase peptides and proteins that are related to the phospholipase C subfamily, nucleic acid sequences in the form of transcript sequences, cDNA sequences and/or genomic sequences that encode these phospholipase peptides and proteins, nucleic acid variation (allelic information), tissue distribution of expression, and information about the closest art known protein/peptide/domain that has structural or sequence homology to the phospholipase of the present invention.

In addition to being previously unknown, the peptides that are provided in the present invention are selected based on their ability to be used for the development of commercially important products and services. Specifically, the present peptides are selected based on homology and/or structural relatedness to known phospholipase proteins of the phospholipase C subfamily and the expression pattern observed. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known phospholipase C family or subfamily of phospholipase proteins.

Specific Embodiments

Peptide Molecules

The present invention provides nucleic acid sequences that encode protein molecules that have been identified as being members of the phospholipase family of proteins and are related to the phospholipase C subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phospholipase peptides of the present invention, phospholipase peptides, or peptides/proteins of the present invention.

The present invention provides isolated peptide and protein molecules that consist of, consist essentially of, or comprise the amino acid sequences of the phospholipase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phospholipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phospholipase peptide can be purified from cells that naturally express it, purified from cells that have been altered to express it (recombinant), or synthesized using known protein synthesis methods. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. For example, a nucleic acid molecule encoding the phospholipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phospholipase peptides of the present invention are the naturally occurring mature proteins. A brief description of how various types of these proteins can be made/isolated is provided below.

The phospholipase peptides of the present invention can be attached to heterologous sequences to form chimeric or fusion proteins. Such chimeric and fusion proteins comprise a phospholipase peptide operatively linked to a heterologous protein having an amino acid sequence not substantially homologous to the phospholipase peptide. "Operatively linked" indicates that the phospholipase peptide and the heterologous protein are fused in-frame. The heterologous protein can be fused to the N-terminus or C-terminus of the phospholipase peptide.

In some uses, the fusion protein does not affect the activity of the phospholipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phospholipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al, *Current Protocols in Molecular Biology*, 1992). Moreover, many expression vectors are commercially available that already encode a fusion moiety (e.g., a GST protein). A phospholipase peptide-encoding nucleic acid can be cloned into such an expression vector such that the fusion moiety is linked in-frame to the phospholipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phospholipase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phospholipase peptides of the present invention as well as being encoded by the same genetic locus as the phospholipase peptide provided herein. The gene encoding the novel phospholipase protein of the present invention is located on a genome component that has been mapped to human chromosome 17 (as indicated in FIG. 3), which is supported by multiple lines of evidence, such as STS and BAC map data.

Allelic variants of a phospholipase peptide can readily be identified as being a human protein having a high degree (significant) of sequence homology/identity to at least a portion of the phospholipase peptide as well as being encoded by the same genetic locus as the phospholipase peptide provided herein. Genetic locus can readily be determined based on the genomic information provided in FIG. 3, such as the genomic sequence mapped to the reference human. The gene encoding the novel phospholipase protein of the present invention is located on a genome component that has been mapped to human chromosome 17 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phospholipase peptide encoding nucleic acid molecule under stringent conditions as more fully described below.

FIG. 3 provides information on SNPs that have been found in the gene encoding the phospholipase proteins of the present invention. SNPs were identified at 16 different nucleotide positions. SNPs outside the ORF and in introns may affect control/regulatory elements.

Paralogs of a phospholipase peptide can readily be identified as having some degree of significant sequence homology/identity to at least a portion of the phospholipase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phospholipase peptide encoding nucleic acid molecule under moderate to stringent conditions as more fully described below.

Orthologs of a phospholipase peptide can readily be identified as having some degree of significant sequence homology/identity to at least a portion of the phospholipase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phospholipase peptide encoding nucleic acid molecule under moderate to stringent conditions, as more fully described below, depending on the degree of relatedness of the two organisms yielding the proteins.

Non-naturally occurring variants of the phospholipase peptides of the present invention can readily be generated using recombinant techniques. Such variants include, but are not limited to deletions, additions and substitutions in the amino acid sequence of the phospholipase peptide. For example, one class of substitutions are conserved amino acid substitution. Such substitutions are those that substitute a given amino acid in a phospholipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phospholipase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phospholipase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol* 224:899–904 (1992); de Vos et al. *Science* 255:306–312 (1992)).

The present invention further provides fragments of the phospholipase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phospholipase peptide. Such fragments can be chosen based on the ability to retain one or more of the biological activities of the phospholipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phospholipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phospholipase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N. Y. Acad. Sci.* 663:48–62 (1992)).

Accordingly, the phospholipase peptides of the present invention also encompass derivatives or analogs in which a substituted amino acid residue is not one encoded by the genetic code, in which a substituent group is included, in which the mature phospholipase peptide is fused with another compound, such as a compound to increase the half-life of the phospholipase peptide (for example, polyethylene glycol), or in which the additional amino acids are fused to the mature phospholipase peptide, such as a leader or secretory sequence or a sequence for purification of the mature phospholipase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phospholipase-effector protein interaction or phospholipase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phospholipases isolated from humans and their human/mammalian orthologs serve as targets for identifying agents for use in mammalian therapeutic applications, e.g. a human drug, particularly in modulating a biological or pathological response in a cell or tissue that expresses the phospholipase. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain. A large percentage of pharmaceutical agents are being developed that modulate the activity of phospholipase proteins, particularly members of the phospholipase C subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Such uses can readily be determined using the information provided herein, that which is known in the art, and routine experimentation.

The proteins of the present invention (including variants and fragments that may have been disclosed prior to the present invention) are useful for biological assays related to phospholipases that are related to members of the phospholipase C subfamily. Such assays involve any of the known phospholipase functions or activities or properties useful for diagnosis and treatment of phospholipase-related conditions that are specific for the subfamily of phospholipases that the one of the present invention belongs to, particularly in cells and tissues that express the phospholipase. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain.

The proteins of the present invention are also useful in drug screening assays, in cell-based or cell-free systems. Cell-based systems can be native, i.e., cells that normally express the phospholipase, as a biopsy or expanded in cell culture. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. In an alternate embodiment, cell-based assays involve recombinant host cells expressing the phospholipase protein.

The polypeptides can be used to identify compounds that modulate phospholipase activity of the protein in its natural state or an altered form that causes a specific disease or pathology associated with the phospholipase. Both the phospholipases of the present invention and appropriate variants and fragments can be used in high-throughput screens to assay candidate compounds for the ability to bind to the phospholipase. These compounds can be further screened against a functional phospholipase to determine the effect of the compound on the phospholipase activity. Further, these compounds can be tested in animal or invertebrate systems to determine activity/effectiveness. Compounds can be identified that activate (agonist) or inactivate (antagonist) the phospholipase to a desired degree.

Further, the proteins of the present invention can be used to screen a compound for the ability to stimulate or inhibit interaction between the phospholipase protein and a molecule that normally interacts with the phospholipase protein, e.g. a substrate or a component of the signal pathway that the phospholipase protein normally interacts (for example, another phospholipase). Such assays typically include the steps of combining the phospholipase protein with a candidate compound under conditions that allow the phospholipase protein, or fragment, to interact with the target molecule, and to detect the formation of a complex between the protein and the target or to detect the biochemical consequence of the interaction with the phospholipase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3)

antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phospholipases or appropriate fragments containing mutations that affect phospholipase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phospholipase activity. The assays typically involve an assay of events in the signal transduction pathway that indicate phospholipase activity. Thus, the phosphorylation of a substrate, activation of a protein, a change in the expression of genes that are up- or down-regulated in response to the phospholipase protein dependent signal cascade can be assayed.

Any of the biological or biochemical functions mediated by the phospholipase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phospholipase can be assayed. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain.

Binding and/or activating compounds can also be screened by using chimeric phospholipase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phospholipase. Accordingly, a different set of signal transduction components is available as an end-point assay for activation. This allows for assays to be performed in other than the specific host cell from which the phospholipase is derived.

The proteins of the present invention are also useful in competition binding assays in methods designed to discover compounds that interact with the phospholipase (e.g. binding partners and/or ligands). Thus, a compound is exposed to a phospholipase polypeptide under conditions that allow the compound to bind or to otherwise interact with the polypeptide. Soluble phospholipase polypeptide is also added to the mixture. If the test compound interacts with the soluble phospholipase polypeptide, it decreases the amount of complex formed or activity from the phospholipase target. This type of assay is particularly useful in cases in which compounds are sought that interact with specific regions of the phospholipase. Thus, the soluble polypeptide that competes with the target phospholipase region is designed to contain peptide sequences corresponding to the region of interest.

To perform cell free drug screening assays, it is sometimes desirable to immobilize either the phospholipase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phospholipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phospholipase-binding protein and a candidate compound are incubated in the phospholipase protein-presenting wells and the amount of complex trapped in the well can be quantitated. Methods for detecting such complexes, in addition to those described above for the GST-immobilized complexes, include immunodetection of complexes using antibodies reactive with the phospholipase protein target molecule, or which are reactive with phospholipase protein and compete with the target molecule, as well as enzyme-linked assays which rely on detecting an enzymatic activity associated with the target molecule.

Agents that modulate one of the phospholipases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phospholipase protein activity identified according to these drug screening assays can be used to treat a subject with a disorder mediated by the phospholipase pathway, by treating cells or tissues that express the phospholipase. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. These methods of treatment include the steps of administering a modulator of phospholipase activity in a pharmaceutical composition to a subject in need of such treatment, the modulator being identified as described herein.

In yet another aspect of the invention, the phospholipase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phospholipase and are involved in phospholipase activity. Such phospholipase-binding proteins are also likely to be involved in the propagation of signals by the phospholipase proteins or phospholipase targets as, for example, downstream elements of a phospholipase-mediated signaling pathway. Alternatively, such phospholipase-binding proteins are likely to be phospholipase inhibitors.

The two-hybrid system is based on the modular nature of most transcription factors, which consist of separable DNA-binding and activation domains. Briefly, the assay utilizes two different DNA constructs. In one construct, the gene that codes for a phospholipase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phospholipase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phospholipase protein.

This invention further pertains to novel agents identified by the above-described screening assays. Accordingly, it is within the scope of this invention to further use an agent identified as described herein in an appropriate animal model. For example, an agent identified as described herein (e.g., a phospholipase-modulating agent, an antisense phospholipase nucleic acid molecule, a phospholipase-specific antibody, or a phospholipase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phospholipase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. The method involves contacting a biological sample with a compound capable of interacting with the phospholipase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phospholipase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phospholipase protein in which one or more of the phospholipase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phospholipase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Accordingly, methods for treatment include the use of the phospholipase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phospholipase proteins. Antibodies can be prepared from any region of the peptide as described herein. However, preferred regions will include those involved in function/activity and/or phospholipase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Thus, where a specific protein has been correlated with expression in a specific tissue, antibodies that are specific for this protein can be used to identify a tissue type.

The antibodies are also useful for inhibiting protein function, for example, blocking the binding of the phospholipase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phospholipase peptide or protein of the present invention (cDNA, transcript and genomic sequence). Such nucleic acid molecules will consist of, consist essentially of, or comprise a nucleotide sequence that encodes one of the phospholipase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phospholipase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the phospholipase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phospholipase protein of the present invention is located on a genome component that has been mapped to human chromosome 17 (as indicated in FIG. 3), which is supported by multiple lines of evidence, such as STS and BAC map data.

FIG. 3 provides information on SNPs that have been found in the gene encoding the phospholipase proteins of the present invention. SNPs were identified at 16 different nucleotide positions. SNPs outside the ORF and in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6X sodium chloride/sodium citrate (SSC) at about 45 C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 16 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phospholipase protein of the present invention is located on a genome component that has been mapped to human chromosome 17 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phospholipase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phospholipase protein, such as by measuring a level of a phospholipase-encoding nucleic acid in a sample of cells from a subject e.g., mRNA or genomic DNA, or determining if a phospholipase gene has been mutated. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain.

Nucleic acid expression assays are useful for drug screening to identify compounds that modulate phospholipase nucleic acid expression.

The invention thus provides a method for identifying a compound that can be used to treat a disorder associated with nucleic acid expression of the phospholipase gene, particularly biological and pathological processes that are mediated by the phospholipase in cells and tissues that express it. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. The method typically includes assaying the ability of the compound to modulate the expression of the phospholipase nucleic acid and thus identifying a compound that can be used to treat a disorder characterized by undesired phospholipase nucleic acid expression. The assays can be performed in cell-based and cell-free systems. Cell-based assays include cells naturally expressing the phospholipase nucleic acid or recombinant cells genetically engineered to express specific nucleic acid sequences.

The assay for phospholipase nucleic acid expression can involve direct assay of nucleic acid levels, such as mRNA levels, or on collateral compounds involved in the signal pathway. Further, the expression of genes that are up- or down-regulated in response to the phospholipase protein signal pathway can also be assayed. In this embodiment the regulatory regions of these genes can be operably linked to a reporter gene such as luciferase.

Thus, modulators of phospholipase gene expression can be identified in a method wherein a cell is contacted with a candidate compound and the expression of mRNA determined. The level of expression of phospholipase mRNA in the presence of the candidate compound is compared to the level of expression of phospholipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phospholipase nucleic acid expression in cells and tissues that express the phospholipase. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain. Modulation includes both up-regulation (i.e. activation or agonization) or down-regulation (suppression or antagonization) or nucleic acid expression.

Alternatively, a modulator for phospholipase nucleic acid expression can be a small molecule or drug identified using the screening assays described herein as long as the drug or small molecule inhibits the phospholipase nucleic acid expression in the cells and tissues that express the protein. Experimental data as provided in FIG. 1 indicates expression in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain.

The nucleic acid molecules are also useful for monitoring the effectiveness of modulating compounds on the expression or activity of the phospholipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phospholipase nucleic acid expression, and particularly in qualitative changes that lead to pathology. The nucleic acid molecules can be used to detect mutations in phospholipase genes and gene expression products such as mRNA. The nucleic acid molecules can be used as hybridization probes to detect naturally occurring genetic mutations in the phospholipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phospholipase gene associated with a dysfunction provides a diagnostic tool for an active disease or susceptibility to disease when the disease results from overexpression, underexpression, or altered expression of a phospholipase protein.

Individuals carrying mutations in the phospholipase gene can be detected at the nucleic acid level by a variety of techniques. FIG. 3 provides information on SNPs that have been found in the gene encoding the phospholipase proteins of the present invention. SNPs were identified at 16 different nucleotide positions. SNPs outside the ORF and in introns may affect control/regulatory elements. The gene encoding the novel phospholipase protein of the present invention is located on a genome component that has been mapped to human chromosome 17 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phospholipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phospholipase gene and a wild-type gene can be determined by direct DNA sequencing. A variety of automated sequencing procedures can be utilized when performing the diagnostic assays (Naeve, C. W., (1995) i Biotechniques 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 21 7:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly. the nucleic acid molecules described herein can be used to assess the mutation content of the phospholipase gene in an individual in order to select an appropriate compound or dosage regimen for treatment. FIG. 3 provides information on SNPs that have been found in the gene encoding the phospholipase proteins of the present invention. SNPs were identified at 16 different nucleotide positions. SNPs outside the ORF and in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phospholipase gene expression in cells, tissues, and organisms. A DNA antisense nucleic acid molecule is designed to be complementary to a region of the gene involved in transcription, preventing transcription and hence production of phospholipase protein. An antisense RNA or DNA nucleic acid molecule would hybridize to the mRNA and thus block translation of mRNA into phospholipase protein.

Alternatively, a class of antisense molecules can be used to inactivate mRNA in order to decrease expression of phospholipase nucleic acid. Accordingly, these molecules can treat a disorder characterized by abnormal or undesired phospholipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phospholipase protein, such as substrate binding.

The nucleic acid molecules also provide vectors for gene therapy in patients containing cells that are aberrant in phospholipase gene expression. Thus, recombinant cells, which include the patient's cells that have been engineered ex vivo and returned to the patient, are introduced into an individual where the cells produce the desired phospholipase protein to treat the individual.

The invention also encompasses kits for detecting the presence of a phospholipase nucleic acid in a biological sample. Experimental data as provided in FIG. 1 indicates that phospholipase proteins of the present invention are expressed in humans in pancreas adenocarcinomas, lung, brain anaplastic oligodendrogliomas, placenta choriocarcinomas, pancreas adenocarcinomas, uterus endometrium, colon adenocarcinomas, eye retinoblastomas, and fetal brain. Specifically, a virtual northern blot shows expression in pancreas adenocarcinomas, lung, brain anaplastic oligodendrogliomas, placenta choriocarcinomas, pancreas adenocarcinomas, uterus endometrium, colon adenocarcinomas, and eye retinoblastomas. In addition, PCR-based tissue screening panels indicate expression in fetal brain. For example, the kit can comprise reagents such as a labeled or labelable nucleic acid or agent capable of detecting phospholipase nucleic acid in a biological sample; means for determining the amount of phospholipase nucleic acid in the sample; and means for comparing the amount of phospholipase nucleic acid in the sample with a standard. The compound or agent can be packaged in a suitable container. The kit can further comprise instructions for using the kit to detect phospholipase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251 116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phospholipase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phospholipase gene of the present invention. FIG. 3 provides information on SNPs that have been found in the gene encoding the phospholipase proteins of the present invention. SNPs were identified at 16 different nucleotide positions. SNPs outside the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985), Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phospholipase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophospholipase. Typical fusion expression vectors include pGEX (Smith et al., *Gene* 67:31–40 (1988)), pMAL (New England Biolabs, Beverly, Me.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology. Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al, *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phospholipases, appropriate secretion signals are incorporated into the vector. The signal sequence can be endogenous to the peptides or heterologous to these peptides.

Where the peptide is not secreted into the medium, which is typically the case with phospholipases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a phospholipase protein or peptide that can be further purified to produce desired amounts of phospholipase protein or fragments. Thus, host cells containing expression vectors are useful for peptide production.

Host cells are also useful for conducting cell-based assays involving the phospholipase protein or phospholipase protein fragments, such as those described above as well as other formats known in the art. Thus, a recombinant host cell expressing a native phospholipase protein is useful for assaying compounds that stimulate or inhibit phospholipase protein function.

Host cells are also useful for identifying phospholipase protein mutants in which these functions are affected. If the mutants naturally occur and give rise to a pathology, host cells containing the mutations are useful to assay compounds that have a desired effect on the mutant phospholipase protein (for example, stimulating or inhibiting function) which may not be indicated by their effect on the native phospholipase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phospholipase protein and identifying and evaluating modulators of phospholipase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phospholipase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phospholipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, phospholipase protein activation, and signal transduction, may not be evident from in vitro cell-free or cell-based assays. Accordingly, it is useful to provide non-human transgenic animals to assay in vivo phospholipase protein function, including substrate interaction, the effect of specific mutant phospholipase proteins on phospholipase protein function and substrate interaction, and the effect of chimeric phospholipase proteins. It is also possible to assess the effect of null mutations, that is, mutations that substantially or completely eliminate one or more phospholipase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated nucleic acid molecule encoding a phospholipase C protein consisting of a nucleotide sequence selected from the group consisting of:
   (a) a nucleotide sequence that encodes a protein comprising the an amino acid sequence of SEQ ID NO:2;
   (b) a nucleic acid molecule consisting of the nucleic acid sequence of SEQ. ID NO:1; and
   (c) a nucleic acid molecule consisting of the nucleic acid sequence of SEQ. ID NO:3.

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 1.

* * * * *

UNITED STATES PATENT AND TRADEMARK OFFICE
CERTIFICATE OF CORRECTION

PATENT NO.   : 6,391,606 B1
DATED        : May 21, 2002
INVENTOR(S)  : Guegler et al.

It is certified that error appears in the above-identified patent and that said Letters Patent is hereby corrected as shown below:

<u>Drawings,</u>
Sequence Listing, SEQ ID NO:1, "Ala", "Gly", "Thr", and "Cys" should read as
-- A, G, T, and C --

Signed and Sealed this

Seventeenth Day of February, 2004

JON W. DUDAS
*Acting Director of the United States Patent and Trademark Office*